US010117632B2

(12) United States Patent
Johnson et al.

(10) Patent No.: US 10,117,632 B2
(45) Date of Patent: Nov. 6, 2018

(54) PORTABLE MEDICAL IMAGING SYSTEM WITH BEAM SCANNING COLLIMATOR

(71) Applicant: GLOBUS MEDICAL, INC., Audubon, PA (US)

(72) Inventors: Norbert Johnson, North Andover, MA (US); Robert Stevens, North Chelmsford, MA (US); Hisham Salem, Newton, MA (US); Yuan Cheng, Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/883,211

(22) Filed: Jan. 30, 2018

(65) Prior Publication Data

US 2018/0249981 A1    Sep. 6, 2018

Related U.S. Application Data

(63) Continuation-in-part of application No. 15/180,126, filed on Jun. 13, 2016, which is a continuation-in-part of application No. 15/014,083, filed on Feb. 3, 2016.

(51) Int. Cl.
*A61B 6/00* (2006.01)
*A61B 6/03* (2006.01)
*A61B 6/06* (2006.01)

(52) U.S. Cl.
CPC ............ *A61B 6/54* (2013.01); *A61B 6/035* (2013.01); *A61B 6/06* (2013.01); *A61B 6/4405* (2013.01)

(58) Field of Classification Search
CPC .................................................. A61B 6/4021
See application file for complete search history.

(56) References Cited

U.S. PATENT DOCUMENTS

| 5,354,314 A | 10/1994 | Hardy et al. |
| 5,397,323 A | 3/1995 | Taylor et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |

(Continued)

OTHER PUBLICATIONS

US 8,231,638, 07/2012, Swarup et al. (withdrawn)

*Primary Examiner* — David J Makiya
*Assistant Examiner* — Soorena Kefayati

(57) ABSTRACT

A portable medical imaging system includes a movable station, a detector panel, an X-ray beam transmitter, and a controller. The movable station includes a c-arm having a first end and a second end that are movable along an arc relative to the movable station. The detector panel is attached to the first end of the movable c-arm. The X-ray beam transmitter faces the detector panel and is attached to the second end of the c-arm. The X-ray beam transmitter contains a collimator that forms a window through which an X-ray beam is transmitted toward the detector panel. The collimator is configured to move the widow in a lateral direction across a direction of the arc. The controller is configured to control movement of the window by the collimator to steer the X-ray beam laterally across the detector panel.

17 Claims, 25 Drawing Sheets

(56) References Cited

U.S. PATENT DOCUMENTS

| | | | |
|---|---|---|---|
| 6,012,216 A | 1/2000 | Esteves et al. | |
| 6,033,415 A | 3/2000 | Mittelstadt et al. | |
| 6,080,181 A | 6/2000 | Jensen et al. | |
| 6,106,511 A | 8/2000 | Jensen | |
| 6,113,264 A * | 9/2000 | Watanabe | A61B 6/466 |
| | | | 378/196 |
| 6,122,541 A | 9/2000 | Cosman et al. | |
| 6,157,853 A | 12/2000 | Blume et al. | |
| 6,167,145 A | 12/2000 | Foley et al. | |
| 6,167,292 A | 12/2000 | Badano et al. | |
| 6,201,984 B1 | 3/2001 | Funda et al. | |
| 6,205,411 B1 | 3/2001 | DiGioia, III et al. | |
| 6,212,419 B1 | 4/2001 | Blume et al. | |
| 6,231,565 B1 | 5/2001 | Tovey et al. | |
| 6,236,875 B1 | 5/2001 | Bucholz et al. | |
| 6,246,900 B1 | 6/2001 | Cosman et al. | |
| 6,301,495 B1 | 10/2001 | Gueziec et al. | |
| 6,312,435 B1 | 11/2001 | Wallace et al. | |
| 6,314,311 B1 | 11/2001 | Williams et al. | |
| 6,322,567 B1 | 11/2001 | Mittelstadt et al. | |
| 6,325,808 B1 | 12/2001 | Bernard et al. | |
| 6,340,363 B1 | 1/2002 | Bolger et al. | |
| 6,377,011 B1 | 4/2002 | Ben-Ur | |
| 6,379,302 B1 | 4/2002 | Kessman et al. | |
| 6,402,762 B2 | 6/2002 | Hunter et al. | |
| 6,424,885 B1 | 7/2002 | Niemeyer et al. | |
| 6,447,503 B1 | 9/2002 | Wynne et al. | |
| 6,451,027 B1 | 9/2002 | Cooper et al. | |
| 6,477,400 B1 | 11/2002 | Barrick | |
| 6,484,049 B1 | 11/2002 | Seeley et al. | |
| 6,490,467 B1 | 12/2002 | Bucholz et al. | |
| 6,490,475 B1 | 12/2002 | Seeley et al. | |
| 6,499,488 B1 | 12/2002 | Hunter et al. | |
| 6,507,751 B2 | 1/2003 | Blume et al. | |
| 6,535,756 B1 | 3/2003 | Simon et al. | |
| 6,560,354 B1 | 5/2003 | Maurer, Jr. et al. | |
| 6,565,554 B1 | 5/2003 | Niemeyer | |
| 6,587,750 B2 | 7/2003 | Gerbi et al. | |
| 6,614,453 B1 | 9/2003 | Suri et al. | |
| 6,619,840 B2 * | 9/2003 | Rasche | A61B 6/032 |
| | | | 378/196 |
| 6,636,757 B1 | 10/2003 | Jascob et al. | |
| 6,645,196 B1 | 11/2003 | Nixon et al. | |
| 6,669,635 B2 | 12/2003 | Kessman et al. | |
| 6,701,173 B2 | 3/2004 | Nowinski et al. | |
| 6,782,287 B2 | 8/2004 | Grzeszczuk et al. | |
| 6,783,524 B2 | 8/2004 | Anderson et al. | |
| 6,786,896 B1 | 9/2004 | Madhani et al. | |
| 6,788,018 B1 | 9/2004 | Blumenkranz | |
| 6,804,581 B2 | 10/2004 | Wang et al. | |
| 6,823,207 B1 | 11/2004 | Jensen et al. | |
| 6,827,351 B2 | 12/2004 | Graziani et al. | |
| 6,837,892 B2 | 1/2005 | Shoham | |
| 6,839,612 B2 | 1/2005 | Sanchez et al. | |
| 6,856,826 B2 | 2/2005 | Seeley et al. | |
| 6,856,827 B2 | 2/2005 | Seeley et al. | |
| 6,879,880 B2 | 4/2005 | Nowlin et al. | |
| 6,892,090 B2 | 5/2005 | Verard et al. | |
| 6,920,347 B2 | 7/2005 | Simon et al. | |
| 6,968,224 B2 | 11/2005 | Kessman et al. | |
| 6,978,166 B2 | 12/2005 | Foley et al. | |
| 6,991,627 B2 | 1/2006 | Madhani et al. | |
| 6,999,852 B2 | 2/2006 | Green | |
| 7,007,699 B2 | 3/2006 | Martinelli et al. | |
| 7,062,006 B1 | 6/2006 | Pele et al. | |
| 7,063,705 B2 | 6/2006 | Young et al. | |
| 7,072,707 B2 | 7/2006 | Galloway, Jr. et al. | |
| 7,083,615 B2 | 8/2006 | Peterson et al. | |
| 7,097,640 B2 | 8/2006 | Wang et al. | |
| 7,108,421 B2 * | 9/2006 | Gregerson | A61B 6/032 |
| | | | 378/197 |
| 7,130,676 B2 | 10/2006 | Barrick | |
| 7,139,418 B2 | 11/2006 | Abovitz et al. | |
| 7,139,601 B2 | 11/2006 | Bucholz et al. | |
| 7,155,316 B2 | 12/2006 | Sutherland et al. | |
| 7,164,968 B2 | 1/2007 | Treat et al. | |
| 7,167,738 B2 | 1/2007 | Schweikard et al. | |
| 7,169,141 B2 | 1/2007 | Brock et al. | |
| 7,172,627 B2 | 2/2007 | Fiere et al. | |
| 7,239,940 B2 | 7/2007 | Wang et al. | |
| 7,248,914 B2 | 7/2007 | Hastings et al. | |
| 7,302,288 B1 | 11/2007 | Schellenberg | |
| 7,313,430 B2 | 12/2007 | Urquhart et al. | |
| 7,318,827 B2 | 1/2008 | Leitner et al. | |
| 7,319,897 B2 | 1/2008 | Leitner et al. | |
| 7,327,865 B2 | 2/2008 | Fu et al. | |
| 7,331,967 B2 | 2/2008 | Lee et al. | |
| 7,333,642 B2 | 2/2008 | Green | |
| 7,339,341 B2 | 3/2008 | Oleynikov et al. | |
| 7,366,562 B2 | 4/2008 | Dukesherer et al. | |
| 7,379,790 B2 | 5/2008 | Toth et al. | |
| 7,386,365 B2 | 6/2008 | Nixon | |
| 7,422,592 B2 | 9/2008 | Morley et al. | |
| 7,435,216 B2 | 10/2008 | Kwon et al. | |
| 7,440,793 B2 | 10/2008 | Chauhan et al. | |
| 7,466,303 B2 | 12/2008 | Yi et al. | |
| 7,493,153 B2 | 2/2009 | Ahmed et al. | |
| 7,505,617 B2 | 3/2009 | Fu et al. | |
| 7,533,892 B2 | 5/2009 | Schena et al. | |
| 7,542,791 B2 | 6/2009 | Mire et al. | |
| 7,555,331 B2 | 6/2009 | Viswanathan | |
| 7,567,834 B2 | 7/2009 | Clayton et al. | |
| 7,594,912 B2 | 9/2009 | Cooper et al. | |
| 7,606,613 B2 | 10/2009 | Simon et al. | |
| 7,607,440 B2 | 10/2009 | Coste-Maniere et al. | |
| 7,630,752 B2 | 12/2009 | Viswanathan | |
| 7,630,753 B2 | 12/2009 | Simon et al. | |
| 7,643,862 B2 | 1/2010 | Schoenefeld | |
| 7,660,623 B2 | 2/2010 | Hunter et al. | |
| 7,661,881 B2 | 2/2010 | Gregerson et al. | |
| 7,689,320 B2 | 3/2010 | Prisco et al. | |
| 7,691,098 B2 | 4/2010 | Wallace et al. | |
| 7,702,379 B2 | 4/2010 | Avinash et al. | |
| 7,711,083 B2 * | 5/2010 | Heigl | A61B 6/032 |
| | | | 378/20 |
| 7,711,406 B2 | 5/2010 | Kuhn et al. | |
| 7,720,523 B2 | 5/2010 | Omernick et al. | |
| 7,742,801 B2 | 6/2010 | Neubauer et al. | |
| 7,751,865 B2 | 7/2010 | Jascob et al. | |
| 7,762,825 B2 | 7/2010 | Burbank et al. | |
| 7,763,015 B2 | 7/2010 | Cooper et al. | |
| 7,787,699 B2 | 8/2010 | Mahesh et al. | |
| 7,818,044 B2 | 10/2010 | Dukesherer et al. | |
| 7,819,859 B2 | 10/2010 | Prisco et al. | |
| 7,824,401 B2 | 11/2010 | Manzo et al. | |
| 7,831,294 B2 | 11/2010 | Viswanathan | |
| 7,834,484 B2 | 11/2010 | Sartor | |
| 7,835,557 B2 | 11/2010 | Kendrick et al. | |
| 7,835,778 B2 | 11/2010 | Foley et al. | |
| 7,835,784 B2 | 11/2010 | Mire et al. | |
| 7,840,253 B2 | 11/2010 | Tremblay et al. | |
| 7,840,256 B2 | 11/2010 | Lakin et al. | |
| 7,843,158 B2 | 11/2010 | Prisco | |
| 7,844,320 B2 | 11/2010 | Shahidi | |
| 7,853,305 B2 | 12/2010 | Simon et al. | |
| 7,865,269 B2 | 1/2011 | Prisco et al. | |
| D631,966 S | 2/2011 | Perloff et al. | |
| 7,879,045 B2 | 2/2011 | Gielen et al. | |
| 7,881,767 B2 | 2/2011 | Strommer et al. | |
| 7,881,770 B2 | 2/2011 | Melkent et al. | |
| 7,886,743 B2 | 2/2011 | Cooper et al. | |
| RE42,194 E | 3/2011 | Foley et al. | |
| RE42,226 E | 3/2011 | Foley et al. | |
| 7,907,166 B2 | 3/2011 | Lamprecht et al. | |
| 7,909,122 B2 | 3/2011 | Schena et al. | |
| 7,925,653 B2 | 4/2011 | Saptharishi | |
| 7,930,065 B2 | 4/2011 | Larkin et al. | |
| 7,935,130 B2 | 5/2011 | Willliams | |
| 7,940,999 B2 | 5/2011 | Liao et al. | |
| 7,945,012 B2 | 5/2011 | Ye et al. | |
| 7,953,470 B2 | 5/2011 | Vetter et al. | |
| 7,954,397 B2 | 6/2011 | Choi et al. | |
| 7,971,341 B2 | 7/2011 | Dukesherer et al. | |
| 7,974,674 B2 | 7/2011 | Hauck et al. | |

(56) References Cited

U.S. PATENT DOCUMENTS

| | | |
|---|---|---|
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,035,685 B2 | 10/2011 | Jensen |
| 8,046,054 B2 | 10/2011 | Kim et al. |
| 8,046,057 B2 | 10/2011 | Clarke |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,092,370 B2 | 1/2012 | Roberts et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,120,301 B2 | 2/2012 | Goldberg et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,238,522 B2 * | 8/2012 | Frey .................. A61B 6/06 378/156 |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,734,432 B2 | 5/2014 | Tuma et al. |

(56) References Cited

U.S. PATENT DOCUMENTS

| | | | |
|---|---|---|---|
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,792,704 B2 | 7/2014 | Isaacs |
| 8,800,838 B2 | 8/2014 | Shelton, IV |
| 8,808,164 B2 | 8/2014 | Hoffman et al. |
| 8,812,077 B2 | 8/2014 | Dempsey |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 9,001,963 B2 | 4/2015 | Sowards-Emmerd et al. |
| 9,380,984 B2 | 7/2016 | Li et al. |
| 9,398,886 B2 | 7/2016 | Gregerson et al. |
| 9,398,890 B2 | 7/2016 | Dong et al. |
| 9,420,975 B2 | 8/2016 | Gutfleisch et al. |
| 9,649,077 B2* | 5/2017 | Bouvier | A61B 6/102 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2004/0222380 A1* | 11/2004 | Fuchs | A61B 6/032 |
| | | | 250/369 |
| 2005/0089134 A1* | 4/2005 | Bruder | A61B 6/032 |
| | | | 378/9 |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0210015 A1 | 9/2006 | Pele et al. |
| 2006/0241416 A1 | 10/2006 | Marquart et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0002806 A1* | 1/2008 | Nishide | A61B 6/032 |
| | | | 378/4 |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0175354 A1* | 7/2008 | Wang | A61B 6/4441 |
| | | | 378/197 |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0022267 A1* | 1/2009 | Kondo | A61B 6/032 |
| | | | 378/15 |
| 2009/0030428 A1 | 1/2009 | Omori et al. |
| 2009/0080737 A1 | 3/2009 | Battle et al. |
| 2009/0180586 A1* | 7/2009 | Fehre | A61B 6/4429 |
| | | | 378/20 |
| 2009/0185655 A1 | 7/2009 | Koken et al. |
| 2009/0213990 A1* | 8/2009 | Bergfjord | A61B 6/032 |
| | | | 378/65 |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0054395 A1* | 3/2010 | Noshi | A61B 6/032 |
| | | | 378/16 |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0096894 A1* | 4/2011 | Uehara | A61B 6/4021 |
| | | | 378/19 |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter |
| 2011/0295062 A1 | 12/2011 | Gratacos Solsona et al. |
| 2011/0295370 A1 | 12/2011 | Suh et al. |
| 2011/0306863 A1* | 12/2011 | Koshnitsky | A61B 5/0555 |
| | | | 600/407 |

(56) References Cited

U.S. PATENT DOCUMENTS

| | | |
|---|---|---|
| 2011/0306986 A1 | 12/2011 | Lee et al. |
| 2012/0046668 A1 | 2/2012 | Gantes |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0155615 A1* | 6/2012 | Liu .................. A61B 6/06 378/150 |
| 2012/0170708 A1* | 7/2012 | Tsubota ............. A61B 6/032 378/7 |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223585 A1* | 8/2013 | Tsukagoshi ......... G01N 23/046 378/4 |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0146948 A1* | 5/2014 | Zhang ................ A61B 6/03 378/147 |
| 2014/0146949 A1* | 5/2014 | Pan .................. A61B 6/06 378/152 |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1* | 7/2014 | Roh ................ A61B 19/2203 600/249 |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2015/0085992 A1* | 3/2015 | Grady ................ A61B 6/4405 378/198 |
| 2015/0092917 A1* | 4/2015 | Roessl ............... A61B 6/032 378/62 |
| 2015/0146847 A1* | 5/2015 | Liu ................ G01N 23/043 378/42 |
| 2015/0164444 A1* | 6/2015 | Grasruck ............ A61B 6/032 378/20 |
| 2015/0173692 A1* | 6/2015 | Heuscher ............ A61B 6/06 378/4 |
| 2015/0196262 A1* | 7/2015 | Grady ............... A61B 6/4441 378/42 |
| 2015/0272531 A1* | 10/2015 | Kieft ................ A61B 6/06 378/147 |
| 2016/0005194 A1 | 1/2016 | Schretter |
| 2016/0074003 A1* | 3/2016 | Manke ............... A61B 6/08 378/206 |
| 2016/0081636 A1* | 3/2016 | Kremer .............. A61B 6/06 378/62 |
| 2016/0166329 A1 | 6/2016 | Langan et al. |
| 2016/0228074 A1* | 8/2016 | Riddell .............. A61B 6/06 |
| 2016/0331335 A1 | 11/2016 | Gregerson et al. |
| 2017/0181716 A1* | 6/2017 | Koehler .............. A61B 6/032 |

* cited by examiner

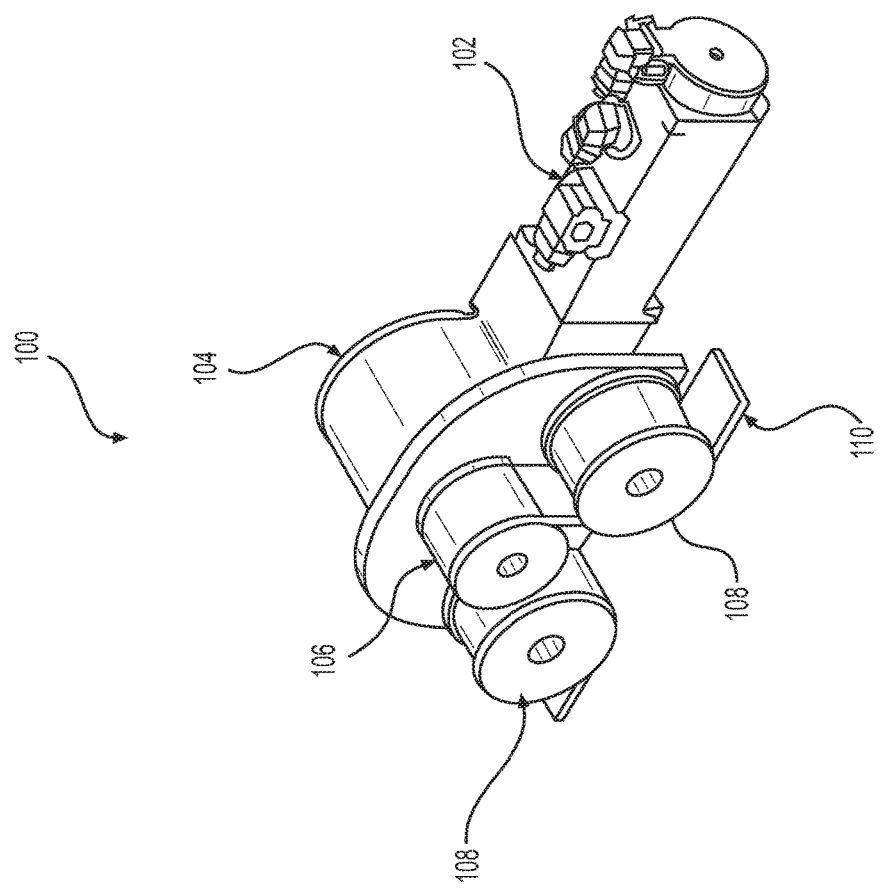

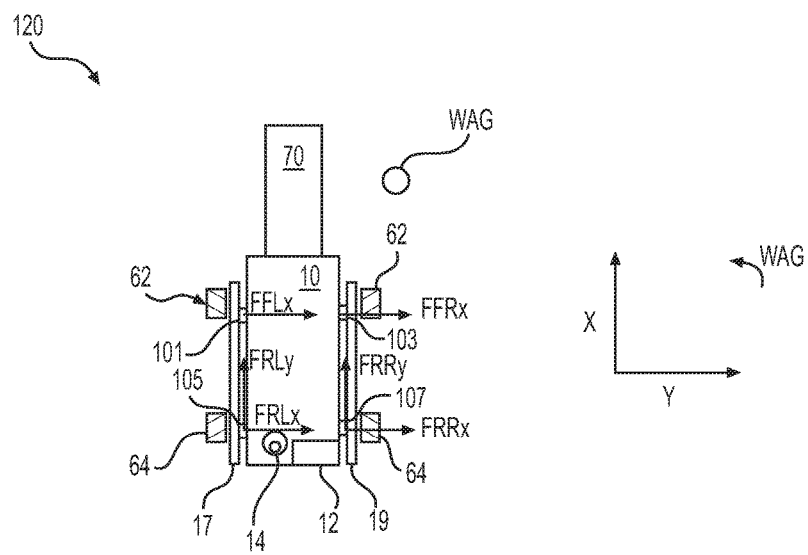
FIG. 10
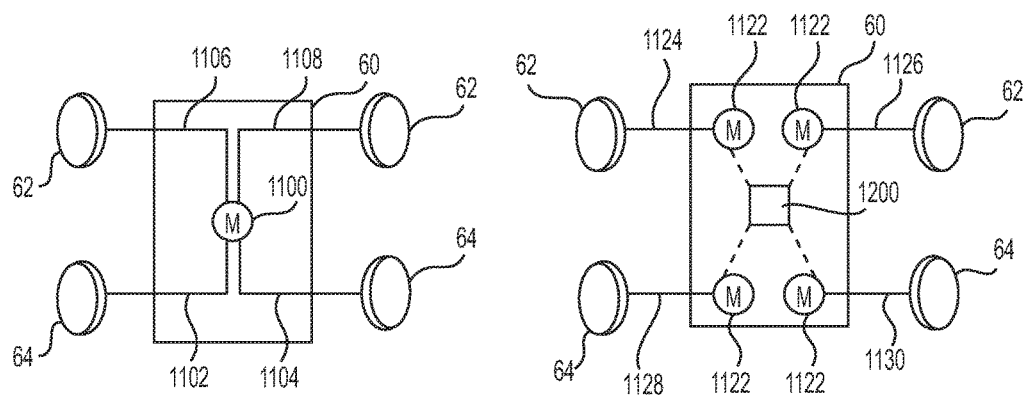
FIG. 11A     FIG. 11B

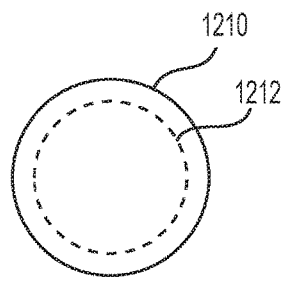
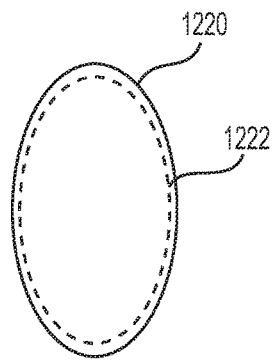
FIG. 12A  FIG. 12B
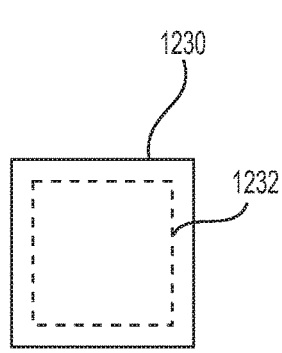
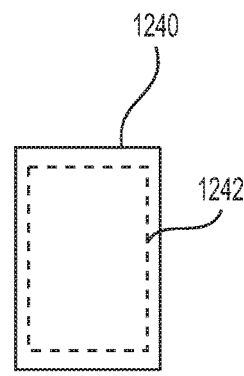
FIG. 12C  FIG. 12D

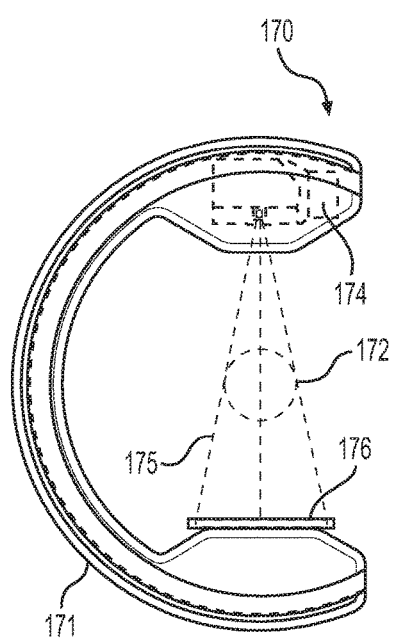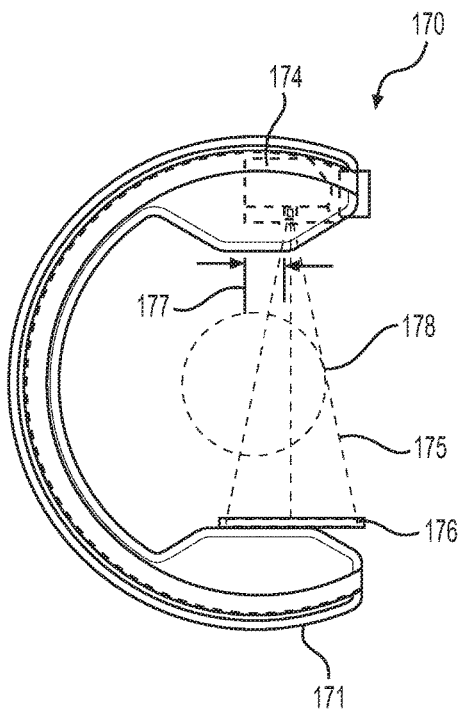
FIG. 17A  FIG. 17B
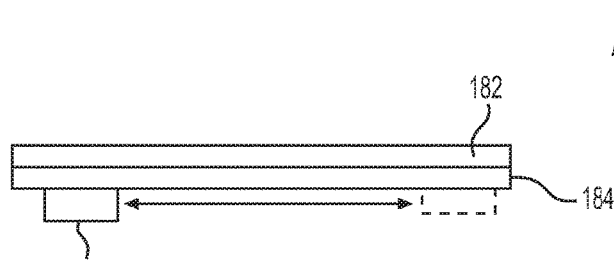
FIG. 18A
FIG. 18B

PORTABLE MEDICAL IMAGING SYSTEM WITH BEAM SCANNING COLLIMATOR

CROSS REFERENCE TO RELATED APPLICATIONS

This application is a continuation-in-part of U.S. patent Ser. No. 15/180,126, filed Jun. 13, 2016, which is a continuation-in-part of U.S. patent Ser. No. 15/014,083, filed Feb. 3, 2016, each of which are hereby incorporated by reference in their entirety for all purposes.

TECHNICAL FIELD

The present disclosure relates to medical imaging systems, and more particularly, controlled movement of the imaging system or components thereof.

BACKGROUND OF THE DISCLOSURE

Healthcare practices have shown the tremendous value of three-dimensional imaging such as computed tomography (CT) imaging, as a diagnostic tool in the Radiology Department. These imaging systems generally contain a fixed bore into which the patient enters from the head or foot. Other areas of care, including the operating room, intensive care departments and emergency departments, rely on two-dimensional imaging (fluoroscopy, ultrasound, 2-D mobile X-ray) as the primary means of diagnosis and therapeutic guidance.

While mobile solutions for 'non-radiology department' and patient-centric 3-D imaging do exist, they are often limited by their freedom of movement to effectively position the system without moving the patient. Their limited freedom of movement has hindered the acceptance and use of mobile three-dimensional imaging systems.

Therefore, there is a need for a small scale and/or mobile three-dimensional imaging systems for use in the operating room, procedure rooms, intensive care units, emergency departments and other parts of the hospital, in ambulatory surgery centers, physician offices, and the military battlefield, which can access the patients in any direction or height and produce high-quality three-dimensional images. These imaging systems may include intra-operative CT and magnetic resonance imaging (MM) scanners, robotic systems to aid in their use or movement. These include systems with 180-degree movement capability ("C-arms") and may also include imaging systems with 360-degree movement capability ("O-arms").

These systems may be very useful during surgery or other procedures when a real-time image is desired to guide operating room personnel. One issue during imaging is the precise positioning of the imaging system. This is especially important in an operating room or operating theatre, in which the size and weight of the imaging equipment and the presence of numerous required personnel make it difficult to precisely position the imaging equipment.

SUMMARY OF THE DISCLOSURE

Some embodiments of the present disclosure are directed to portable medical imaging systems. A portable medical imaging system includes a movable station, a detector panel, an X-ray beam transmitter, and a controller. The movable station includes a c-arm having a first end and a second end that are movable along an arc relative to the movable station. The detector panel is attached to the first end of the movable c-arm. The X-ray beam transmitter faces the detector panel and is attached to the second end of the c-arm. The X-ray beam transmitter contains a collimator that forms a window through which an X-ray beam is transmitted toward the detector panel. The collimator is configured to move the widow in a lateral direction across a direction of the arc. The controller is configured to control movement of the window by the collimator to steer the X-ray beam laterally across the detector panel.

In some further embodiments, the collimator is positioned between an X-ray source and the detector panel. The collimator includes a first pair of shutters that are on opposite sides of the window and which each have an edge surface that forms an opposing edge of the window in the lateral direction. The first pair of shutters are each slidable along respective tracks extending along the lateral direction to change locations of opposing edges of the window. A first pair of motor assemblies are connected to move respective ones of the first pair of opposing shutters along their respective tracks. The controller controls the first pair of motor assemblies to position the first pair of shutters along their respective tracks.

In one embodiment, between each of a plurality of imaging scans through which the X-ray beam transmitter and the detector panel are repetitively moved between spaced apart locations along the arc, the controller may operate to control the first pair of motor assemblies to incrementally move the first pair of shutters in the lateral direction along their respective tracks responsive to a signal indicating completion of the one of the imaging scans.

In another embodiment, the controller controls the first pair of motor assemblies to continuously move the first pair of shutters in a same direction along their respective tracks during an imaging scan while the X-ray beam transmitter and the detector panel are moved between spaced apart locations along the arc to scan the X-ray beam laterally across the detector panel during an imaging scan.

Some further embodiments are directed to the c-arm being configured to change length by telescoping along the arc to change distance along the arc between the connected detector panel and the connected x-ray beam transmitter. Before performing an imaging scan of a cylindrical volume by movement of the X-ray beam transmitter and the detector panel between spaced apart locations along the arc, the controller may operate to control telescoping movement of the c-arm to move at least one of the detector panel and the x-ray beam transmitter along the arc to change distance therebetween and radially shift the cylindrical volume that is imaged during the imaging scan.

The portable medical imaging system may include a translation device that mounts the X-ray beam transmitter to the first end of the c-arm and which is configured to move the X-ray beam transmitter along a rail. Before performing an imaging scan of a cylindrical volume by movement of the X-ray beam transmitter and the detector panel between spaced apart locations along the arc, the controller may operate to control the translation device to position the X-ray beam transmitter in the direction to radially shift the cylindrical volume that is imaged during the imaging scan.

Some further embodiments are directed to the portable medical imaging system including a filter ladder having a support structure and a movable elongated strip. The support structure is connected to the collimator. The movable elongated strip is slideably connected to the support structure. The filter ladder includes X-ray filters that provide different levels of X-ray filtering and which are attached to the movable elongated strip. A light source is attached to the movable elongated strip at a location spaced apart from the X-ray filters. The movable elongated strip is configured to be slidable across the window to sequentially align different ones of the X-ray filters and the light source with the window. The light source is configured to project visible light toward the detector panel when aligned with the window.

Some other embodiments of the present disclosure are directed to related controllers for operating portable medical imaging systems.

It is noted that aspects described with respect to one embodiment disclosed herein may be incorporated in different embodiments although not specifically described relative thereto. That is, all embodiments and/or features of any embodiments can be combined in any way and/or combination. Moreover, methods, systems, and/or computer program products according to embodiments will be or become apparent to one with skill in the art upon review of the following drawings and detailed description. It is intended that all such additional methods, systems, and/or computer program products be included within this description and protected by the accompanying claims.

BRIEF DESCRIPTION OF DRAWINGS

Aspects of the present disclosure are illustrated by way of example and are not limited by the accompanying drawings. In the drawings:

FIG. 8 illustrates a motor assembly for telescopically controlling the C-arms of the gantry.

FIG. 10 is a top plan view of a portable medical imaging device equipped with the control system and omni-directional wheels ("omni-wheels") of the present disclosure and depicting a first example of an array of sensors.

FIGS. 11A and 11B depict configurations for applying power to the omni-wheels of the portable station.

FIGS. 12A-12D depict arrays of sensors useful in portable medical imaging equipment.

FIGS. 17A-17B depict another embodiment in which the imaging signal transmitter and imaging signal sensor have another translational degree of freedom.

FIGS. 18A-18B depict additional details that allow the additional degree of freedom.

DETAILED DESCRIPTION

For purposes of this application, the terms "code", "software", "program", "application", "software code", "software module", "module" and "software program" are used interchangeably to mean software instructions that are executable by a processor. A "user" can be a physician, nurse, or other medical professional.

Figure 1:
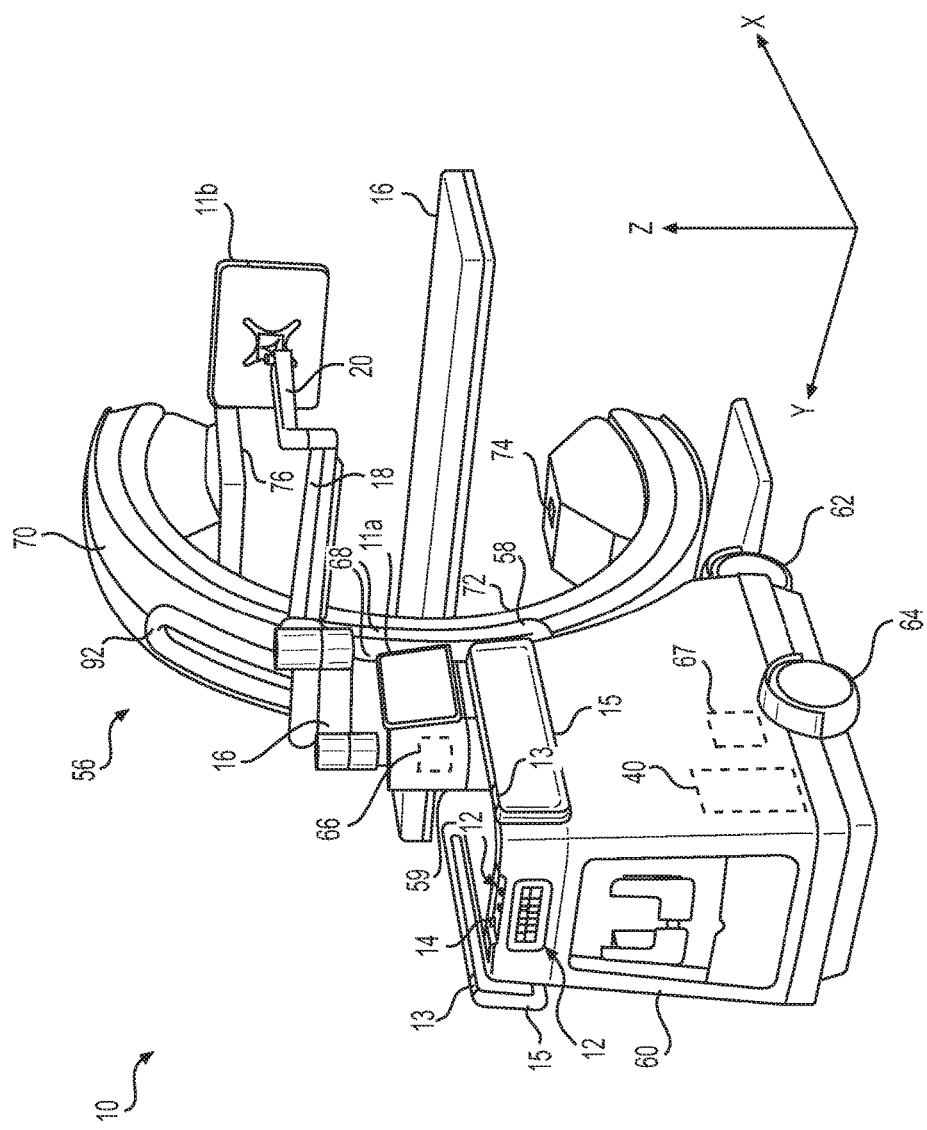
FIG. 1 is a perspective rear view of an imaging system according to one embodiment of the present disclosure.

Turning now to the drawing, FIG. 1 is a schematic diagram showing an imaging system 10, such as a computerized tomographic (CT) x-ray scanner, in accordance with one embodiment of the disclosure. The imaging system 10 includes a movable station 60 and a gantry 56. The movable station includes a vertical shaft 59 and a gantry mount 58 which is rotatably attached to the vertical shaft. The movable station 60 includes two front omni-directional wheels 62 and two rear omni-directional wheels 64, which together provide movement of the movable station 60 in any direction in an X-Y plane. The horizontal X-Y plane is depicted in the Cartesian coordinate system X, Y axes shown in FIG. 1, along with a vertical axis Z. The omni-directional wheels 62, 64 can be obtained, for example, from Active Robots Limited of Somerset, U.K. A pair of handles 13 mounted to the housing of the movable station 60 allow a user to manually maneuver the station.

A motor 66 attached to the vertical shaft 59 is designed to rotate the gantry mount 58 full 360 degrees about the X-axis and a motor 67 moves the gantry mount 58 vertically along the z-axis under the control of the motion control module 51.

The gantry 56 includes a first C-arm 70 slidably coupled to the gantry mount 58 and a second C-arm 72 which is slidably coupled to the first C-arm. In the embodiment shown, the first and second C-arms 70, 72 are outer and inner C-arms, respectively. In the embodiment shown, the outer and inner C-arms 70, 72 are partially-circular in shape and rotate circumferentially about a central axis so as to allow imaging of a patient who is lying in bed 26 without the need to transfer the patient.

An imaging signal transmitter 74 such as an X-ray beam transmitter is mounted to one side of the second C-arm 72 while an imaging sensor 76 such as an X-ray detector array is mounted to the other side of the second C-arm and faces the transmitter. In this example, X-ray transmitter 74 transmits an X-ray beam which is received by X-ray detector or receiver 76 after passing through a relevant portion of a patient (not shown).

In one embodiment, the system 10 is a multi-modality x-ray imaging system designed with surgery in mind. Imaging modalities include, but are not limited to, fluoroscopy, 2D Radiography, and Cone-beam CT. Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (cone beam 3D imaging or cone beam computer tomography) also referred to as C-arm CT, is a medical imaging technique consisting of X-ray computed tomography where the X-rays are divergent, forming a cone. Magnetic resonance imaging (MRI) may also be employed, with suitable precautions for using powerful magnets and controlling the magnetic fields they generate.

The movable station 60 includes an imaging controller system 40 which serves a dual function of (1) controlling the movement of the omni-directional wheels 62, 64, gantry mount 58 and the gantry 56 to position the imaging signal transmitter 74 in relation to the patient, and other component movements as needed, and (2) controlling imaging functions for imaging the patient once proper positioning has been achieved.

Figure 2:
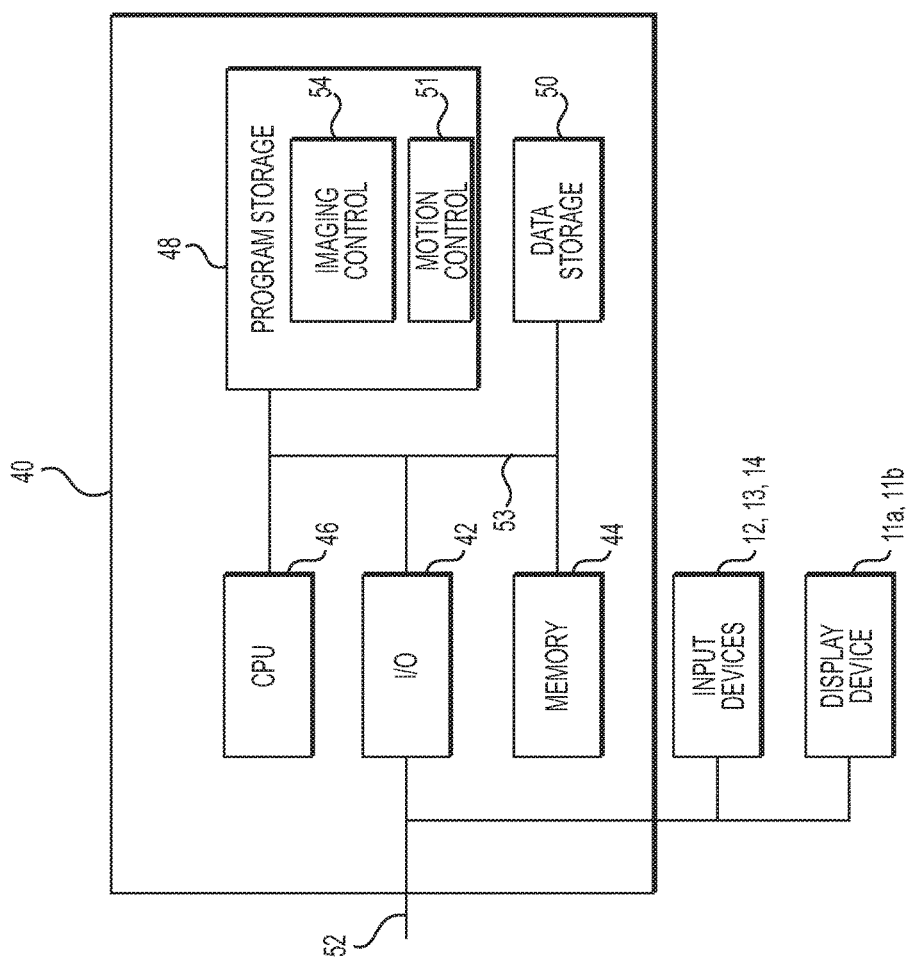
FIG. 2 is a schematic diagram of an imaging controller system 40 according to one embodiment of the present disclosure.

Referring now to FIG. 2, the imaging controller system 40 of the present disclosure is connected to a communication link 52 through an I/O interface 42 such as a USB (universal serial bus) interface, which receives information from and sends information over the communication link 52. The imaging controller system 40 includes memory storage 44 such as RAM (random access memory), processor (CPU) 46, program storage 48 such as ROM or EEPROM, and data storage 50 such as a hard disk, all commonly connected to each other through a bus 53. The program storage 48 stores, among others, imaging control module 54 and motion control module 51, each containing software to be executed by the processor 46. The motion control module 51 executed by the processor 46 controls the wheels 62, 64 of the movable station 60 and various motors in the gantry mount 58 and gantry 56 to position the station 60 near the patient and position the gantry in an appropriate position for imaging a relevant part of the patient. The motion control module may also control additional components used for positioning, as explained below.

The imaging control module 54 executed by the processor 46 controls the imaging signal transmitter 74 and detector array 76 to image the patient body. In one embodiment, the imaging control module images different planar layers of the body and stores them in the memory 44. In addition, the imaging control module 54 can process the stack of images stored in the memory 44 and generate a three dimensional image. Alternatively, the stored images can be transmitted to a host system (not shown) for image processing.

The motion control module 51 and imaging control module 54 include a user interface module that interacts with the user through the display devices 11a and 11b and input devices such as keyboard and buttons 12 and joy stick 14. Strain gauges 13 mounted to the handles 15 are coupled to the I/O device 42 and conveniently provide movement of the movable station 12 in any direction (X, Y, Wag) while the user is holding the handles 15 by hand, as will be discussed in more detail below. The user interface module assists the user in positioning the gantry 56. Any of the software program modules in the program storage 48 and data from the data storage 50 can be transferred to the memory 44 as needed and is executed by the CPU 46. The display device 11a is attached to the housing of the movable station 60 near the gantry mount 58 and display device 11b is coupled to the movable station through three rotatable display arms 16, 18 and 20. First display arm 16 is rotatably attached to the movable station 60, second display arm 18 is rotatably attached to the first arm 16 and third display arm 20 is rotatably attached to the second display arm. The display devices 11a, 11b can have touch screens to also serve as input devices through the use of user interface modules in the modules 51 and 54 to provide maximum flexibility for the user.

Navigation markers 68 placed on the gantry mount 58 are connected to the imaging controller system 40 through the link 52. Under the control of the motion control module 51, the markers 68 allow automatic or semi-automatic positioning of the gantry 56 in relation to the patient bed or (operating room) table via a navigation system (not shown). The markers 68 can be optical, electromagnetic or the like. They may also be placed on other convenient and useful places, e.g., on the patient bed, or otherwise, so that the marker or markers will be visible in the images taken and may be used to orient connecting images when more than one image is taken of a patient, or other object to be imaged. The markers may also contribute to merging or coordinating multiple images when more than one image is taken.

Information can be provided by the navigation system to command the gantry 56 or system 10 to precise locations. In one example, a surgeon holds a navigated probe at a desired orientation for the imaging system 10 to acquire a fluoroscopic or radiographic image along that specified trajectory. Advantageously, this will remove the need for scout shots thus reducing x-ray exposure to the patient and operating room (OR) staff. The navigation markers 68 on the gantry 56 will also allow for automatic registration of 2D or 3D images acquired by the system 10. The markers 68 will also allow for precise repositioning of the system 10 in the event the patient has moved. The markers may be radiopaque or made from other material that makes coordination or navigation easy for the imaging specialists or other medical professionals. The navigation probes or markers may be placed as desired, e.g., nearby or on the object to be imaged, so that the markers do not interfere with the imaging or its interpretation.

In the embodiment shown, the system 10 provides a large range of motion in the 6-degrees of freedom ("DOF") described below. Under the control of the motion control module 51, there are two main modes of motion: positioning of the movable station 60 and positioning of the gantry 56. Other positioning modes are described and may also be included.

The movable station 60 positioning is accomplished via the four omni-directional wheels 62, 64. These wheels 62, 64 allow the movable station 60 to be positioned in all three DOF about the horizontal plane (X, Y, Wag). "Wag" is a system 10 rotation about the vertical axis (Z-axis), "X" is a system forward and backward positioning along the X-axis, and "Y" is system 10 lateral motion along the Y-axis. Under the control of the control module 51, the system 10 can be positioned in any combination of X, Y, and Wag (Wag about any arbitrary Z-axis due to use of omni-directional wheels 62, 64) with unlimited range of motion. In particular, the omni-directional wheels 62, 64 allow for positioning in tight spaces, narrow corridors, or for precisely traversing up and down the length of an OR table or patient bed.

The gantry 56 positioning is accomplished about (Z, Tilt, Rotor). "Z" is gantry 56 vertical positioning, "Tilt" is rotation about the horizontal axis parallel to the X-axis as described above, and "Rotor" is rotation about the horizontal axis parallel to the Y-axis as described above.

Together with the movable station 60 positioning and gantry 56 positioning, the system 10 provides a range of motion in six DOF (X, Y, Wag, Z, Tilt and Rotor) to place the movable station 60 and the imaging transmitter 74 and sensor 76 precisely where they are needed. Advantageously, 3-D imaging can be performed regardless of whether the patient is standing up, sitting up or lying in bed and without having to move the patient.

Precise positions of the system 10 can be stored in the storage memory 50 and recalled at any time by the motion control module 51. This is not limited to gantry 56 positioning but also includes system 10 positioning due to the omni-directional wheels 62, 64, and other axes of motion, as described below.

Figure 3:
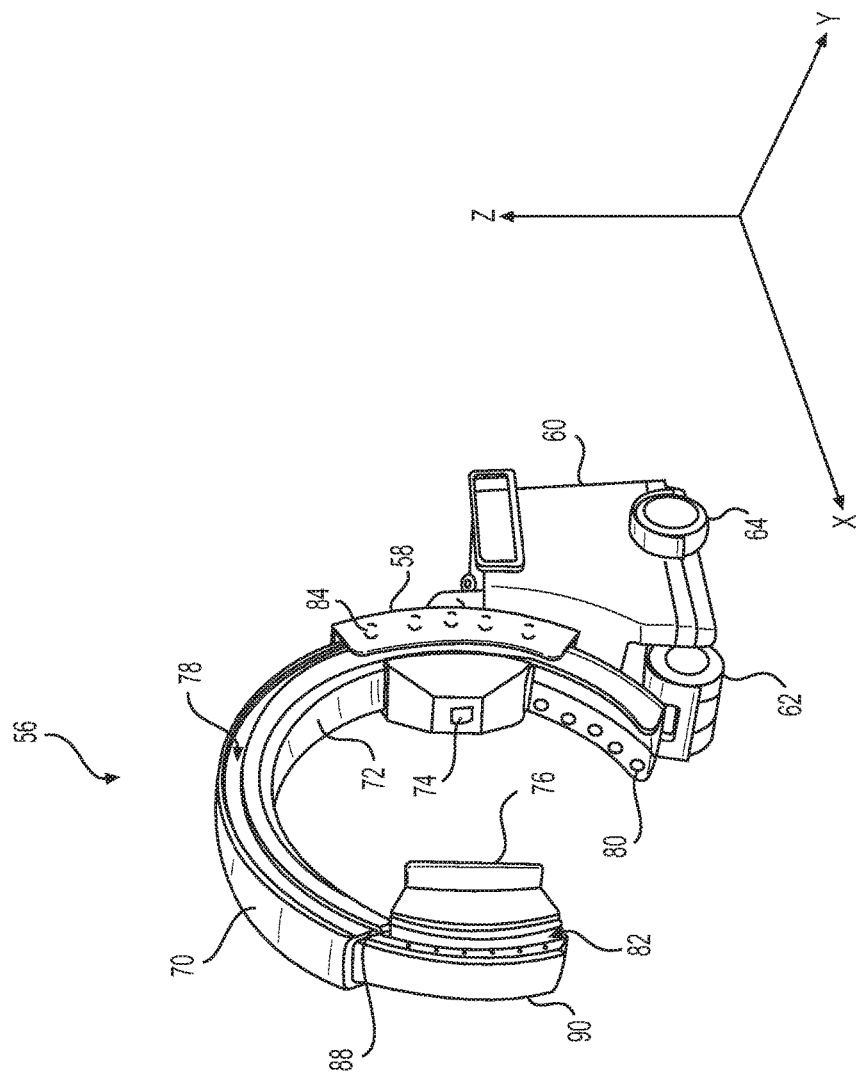
FIG. 3 is a perspective front view of the imaging system of FIG. 1.

As shown in FIG. 3, each of the gantry mount 58, outer C-arm 70 and inner C-arm 72 respectively has a pair of side frames 86, 88, 90 that face each other. A plurality of uniformly spaced rollers 84 are mounted on the inner sides of the side frames 86 of the gantry mount 58. The outer C-arm 70 has a pair of guide rails 78 on the outer sides of the side frames 88. The rollers 84 are coupled to the guide rails 78. As shown, the rollers 84 and the guide rails 78 are designed to allow the outer C-arm 70 to telescopically slide along the gantry mount 58 so as to allow at least 180 degree rotation of the C-arm about its central axis relative to the gantry mount.

A plurality of uniformly spaced rollers 80 are mounted on the inner sides of the side frames 88 of the outer C-arm 70. The inner C-arm 70 has a pair of guide rails 82 on the outer sides of the side frames 90. The rollers 80 are coupled to the guide rails 82. As shown, the rollers 80 and the guide rails 82 are designed to allow the inner C-arm 72 to telescopically slide along the outer C-arm 70 so as to allow at least 180 degree rotation of the C-arm about its central axis relative to the outer C-arm.

Thus, the present disclosure as disclosed herein advantageously allows the gantry 56 to rotate about its central axis a full 360 degrees to provide the maximum flexibility in positioning the imaging system 10 with minimum disturbance of the patient.

Figure 5:
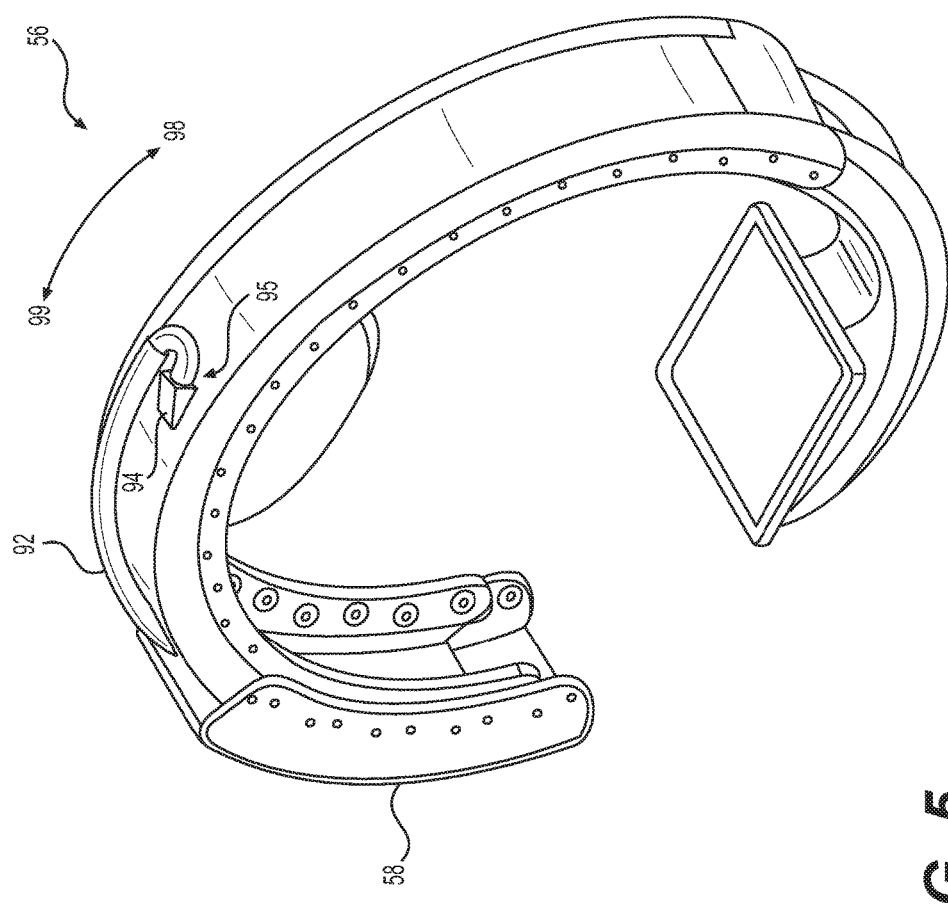
FIG. 5 is a perspective view of the gantry partially showing a cabling arrangement.
Figure 6:
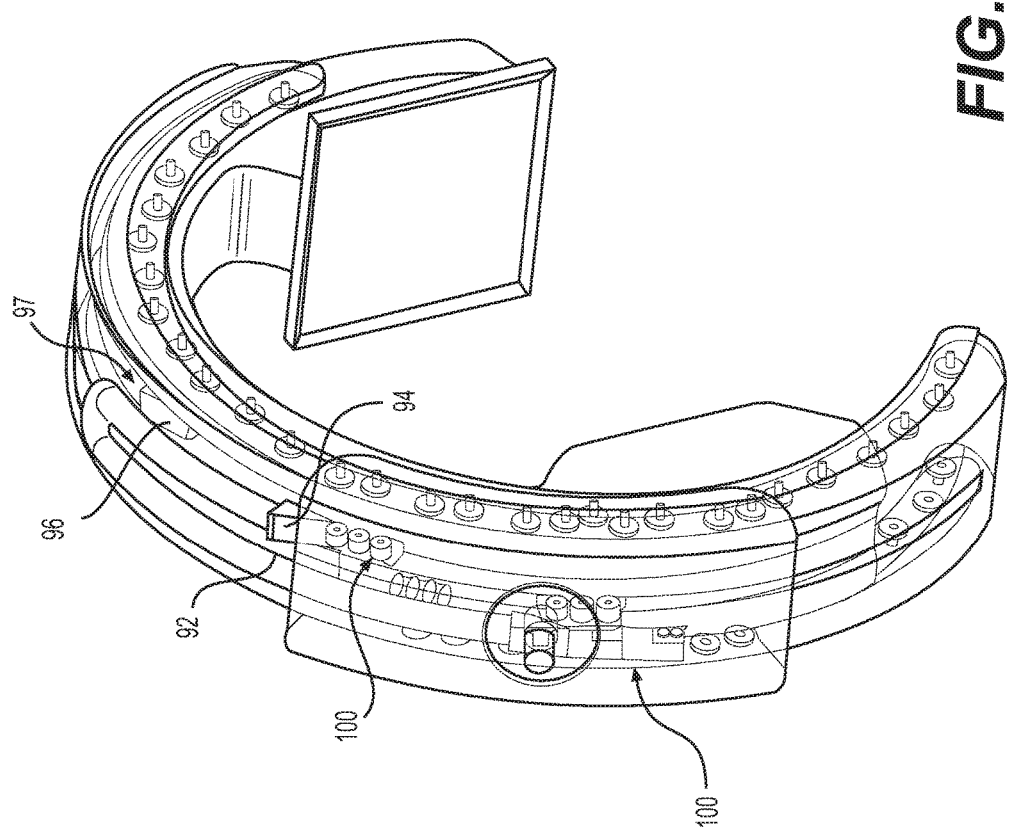
FIG. 6 is a perspective view of the gantry showing the cabling arrangement.
Figure 7:
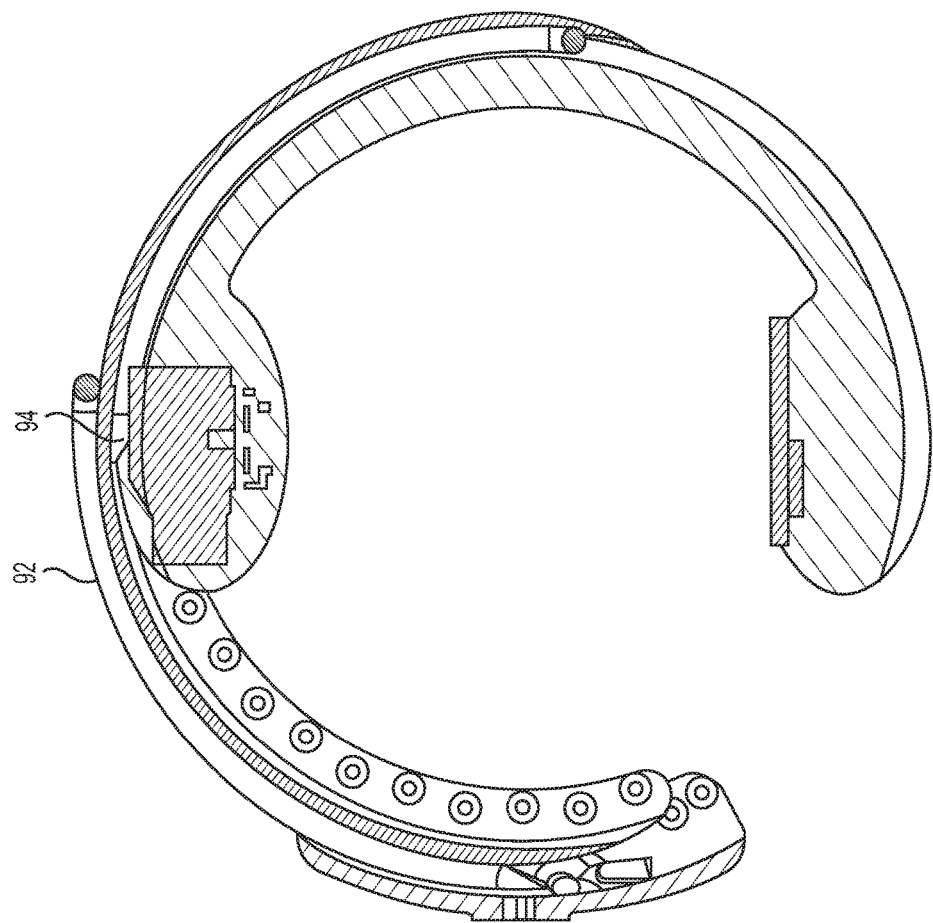
FIG. 7 is a side view of the gantry showing the cabling arrangement.

In another aspect of the present disclosure, a unique cabling arrangement is provided to make the imaging system 10 more compact and visually more appealing. As shown in FIGS. 5 and 6, a cable carrier/harness 92 contains electrical cables to carry signals between the imaging controller system 40 and various motors, X-ray transmitter 74, imaging sensor or detector 76 and various electronic circuits in the gantry 56. A first cable router 94 is mounted to the outer surface of the outer C-arm 70 and a second cable router 96 is mounted to the outer surface of the inner C-arm 72. Each cable router 94, 96 has a through-hole 95, 97 through which the cable carrier 92 passes.

The cable carrier 92 extends from the gantry mount 56 over the outer surface of the first C-arm 70, through the through-hole 95 of the first cable router 94 and over an outer surface of the second C-arm 72. The cable carrier 92 overlying the first C-arm 70 extends in a first circumferential direction (clock-wise as shown) 98 and enters the first cable router 94 in a second circumferential direction (counter clock-wise as shown) 99 opposite to the first circumferential direction to create a 180 degree service loop over the outer surface of the first C-arm.

From there, the cable carrier 92 extends in the first circumferential direction 98 and enters the second cable router in the second circumferential direction 99 to create another service loop over the outer surface of the second C-arm 72.

The particular locations of the first and second cable routers 94, 96 combined with the service loops allow slack in the cable carrier 92 to provide the gantry 56 with full 360 degrees rotation without tangling or causing stress in the cable carrier. In the embodiment shown, the routers are mounted near the midpoint of the C-arms.

FIG. 8 illustrates one embodiment of a motor assembly 100 useful for telescopically rotating the outer C-arm 70 relative to the gantry mount 58 and for rotating the inner C-arm 72 relative to the outer C-arm. Each motor assembly 100 includes a servo motor 102 with encoder feedback, gear box 104 to change the turning ratio, drive pulley 106, idler pulleys 108 and belt 110 threaded between the drive pulley and the idler pulleys. One motor assembly 100 is mounted to the gantry mount to move the outer C-arm 70 relative to the gantry mount and another motor assembly is mounted to the outer C-arm 70 near the center of the arm to move the inner C-arm 70 relative to the outer C-arm.

Figure 9A:
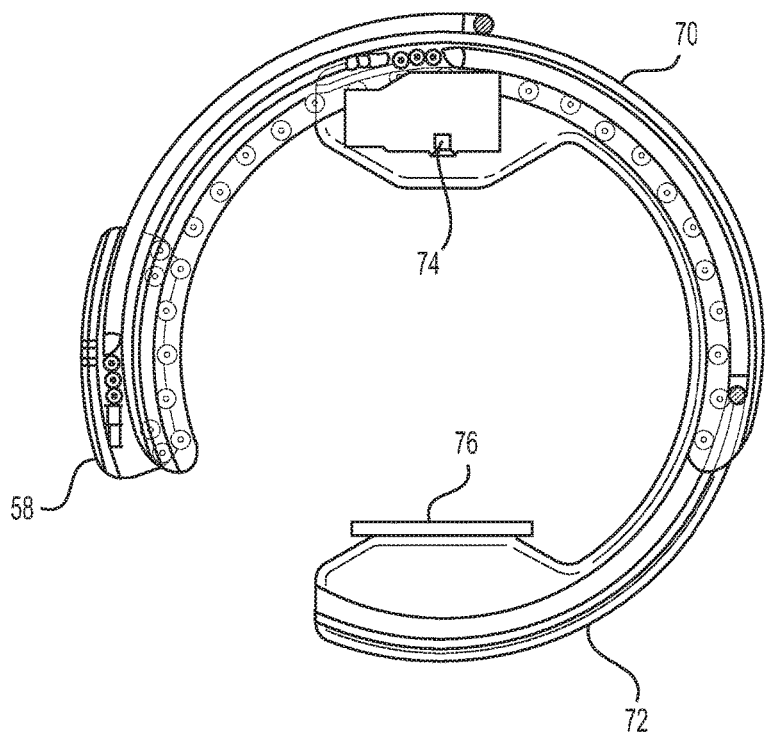
FIGS. 9A-9G illustrate the 360 degree rotation of the gantry in 60 degree increments.
Figure 9B:
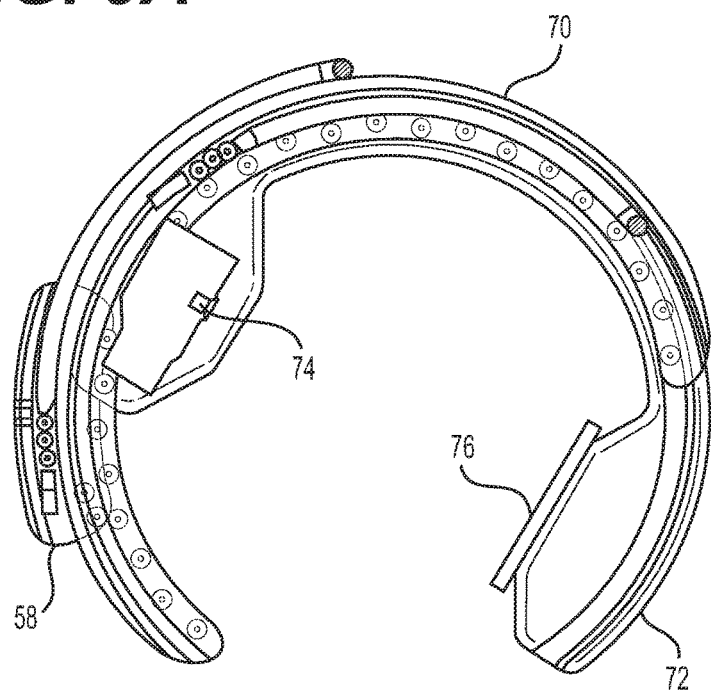
Figure 9C:
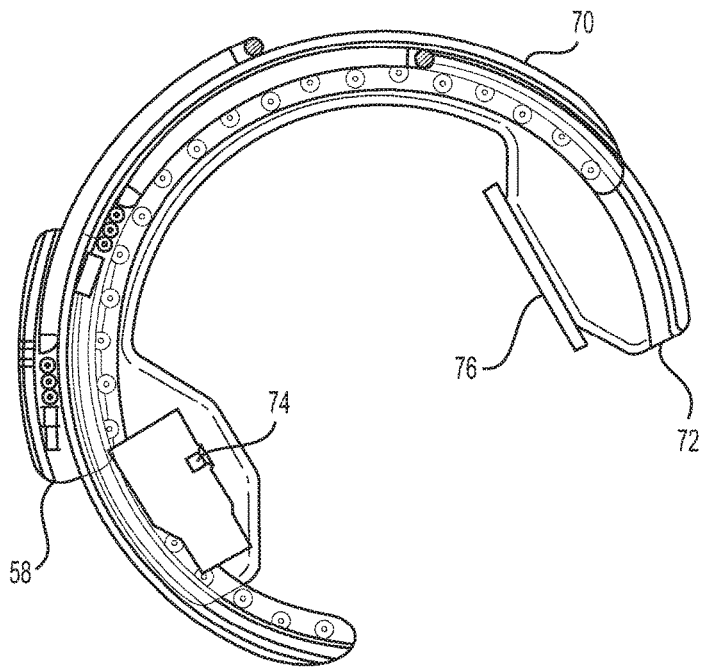
Figure 9D:
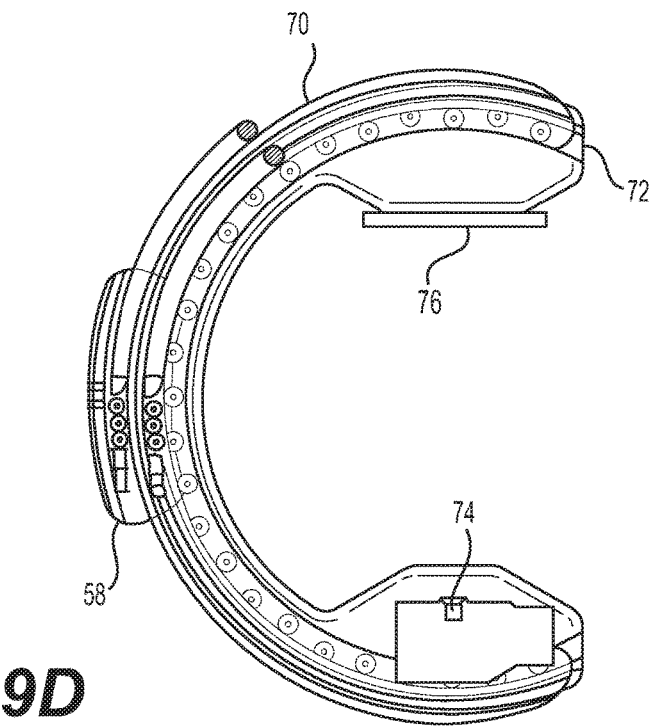
Figure 9E:
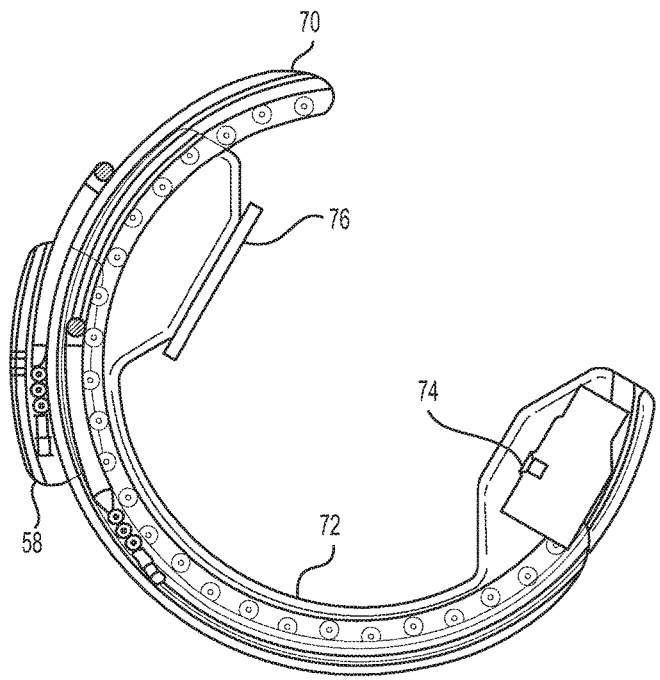
Figure 9F:
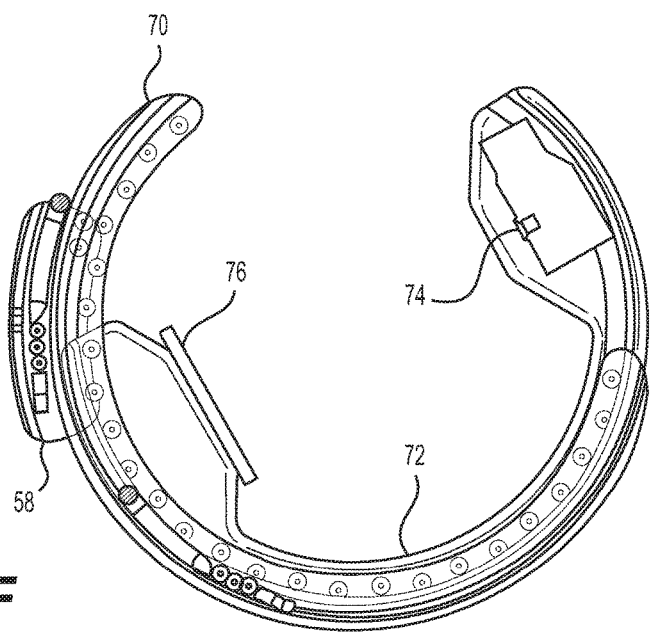
Figure 9G:
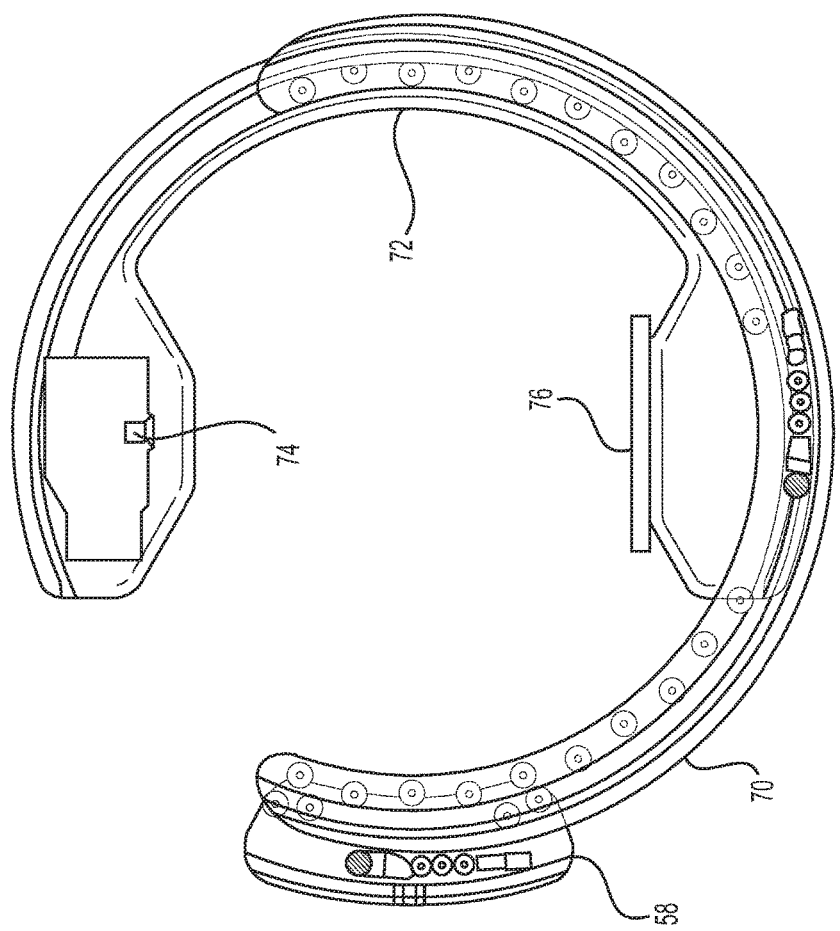

FIGS. 9A-9G illustrate the 360 degree rotation of the gantry 56 in the counter-clockwise direction in 60 degree increments, with FIG. 9A representing a zero degree position of the imaging sensor 76 and transmitter 74. FIG. 9B represents a 60 degree turn/position of the gantry 56. For each 60 degree turn of the gantry 56, the motor assemblies 100, under the control of the motion control module 51, turn the inner C-arm 72 by 30 degrees counter-clock wise and also turn the outer C-arm 70 by 30 degrees counter-clock wise for a combined 60 degree turn. FIG. 9G represents a full 360 degree turn of the gantry 56. As can be seen, the outer C-arm 70 and inner C-arm 72 have each moved 180 degrees from the original zero degree position of FIG. 9A. Note that the transmitter 74 and sensor 76 in FIGS. 9D and 9G are reversed from their positions in FIGS. 1 and 9A. This may be advantageous, for example, if there is an advantage in having the transmitter on one particular side or in having the sensor on one particular side. These orientations are made possible and facile with the present disclosure.

As described above in detail, the present disclosure in various embodiments provide the following benefits: (1) movement of the system in any X-Y direction with Wag-rotation about any Z-axis using omni-directional wheels 62, 64; (2) double telescoping C-gantry for full 360-degree imaging beam rotation; (3) imaging while lying in bed, sitting or standing such as standing CBCT; (4) storage and recall of system 10 and gantry 56 positions; (5) quasi-simultaneous multi-planar x-ray imaging; and (6) recall of positions via robotics or navigation coordinates.

The control system for the portable medical imaging system was described above in FIG. 2. The control system for the sensor-controlled movement of the portable medical imaging system is further explained here with reference to FIG. 2 and FIG. 10. Imaging controller system 40 includes both a motion control portion 51 and an imaging control portion 54. Input devices may include a keyboard with function keys 12, handles 13 and a joystick 14. Any of these input devices may control either or both of the motion control portion 51 and the imaging control portion 54. Switching between a motion control mode and an imaging control mode may be accomplished by a function key, a touch screen command from one of the display devices, or other desired method. The portable medical imaging system may also include, as part of the motion control portion 51 or the input/output 42 a smart phone or cellular phone link or global positioning system (GPS) that may be useful for communicating information concerning a position of the patient or the imaging system via communication link 52.

Control system 120 of FIG. 10 is depicted as a plan view of the portable imaging control system 10, depicting a top view of the imaging system 10 and first C-arm 70. Omni-wheels 62, 64 are separated into front portion omni-wheels 62, left and right, and rear portion omni-wheels 64, also left and right. FIG. 10 also depicts the three axes for the three degrees of omni-wheel freedom of motion of the system. As depicted in the figure, these include freedom to move left or right along a y-axis, freedom to move forward and backward along an x-axis, and freedom of rotation along a rotational axis Wag that is perpendicular to a plane formed by the x and y axes, i.e., a vertical axis. Thus, the vertical axis Wag in FIG. 10 is perpendicular to the plane of the drawing. The vertical rotational axis may be placed as desired with respect to the imaging system since no physical axis of rotation is required. For example, one may program the program storage 48 so that rotational axis Wag coincides with a vertical axis of shaft 59 or the vertical axis of joystick 14. An alternative convenient placement may be the geometrical center of the movable station 60 (see FIG. 1) or a corner of the top of the movable station. Any convenient and useful placement of the axis may be made.

FIG. 10 may also provide a useful reference for a discussion of the sensors used in this disclosure. Left sensors 101, 105 are mounted on the left handle 17 while right sensors 103 and 107 are mounted on the right handle 19. A first embodiment may include these four sensors 101, 103, 105, 107, as shown. A person, such as a health care professional operating the portable imaging device 10, may position the device by using the handles 17, 19 and the motion control portion 51. In one embodiment, the motion control may have two modes, a transport mode and a fine-tune mode. For example, if the portable medical imaging device 10 is transported from one wing of a hospital or other health-care facility, speed may be more highly valued than fine-tuned positioning. Thus, pushing on the rear portion handles 17, 19 of imaging system 10 may activate the transport mode. Pushing on either of the two handles 17, 19 may activate a fine-tune mode, in which every movement of the omni-wheels 62, 64 is slower and more deliberate. Switching between these modes may also be accomplished by appropriate programming allowing the user to switch via a function key, a command, a touch-screen input, and so forth.

In fine tune mode, motion control 51 may be used to return the imaging device 10 to a set position, e.g., snap to a predetermined position. For example, and with reference to FIG. 1, if an imaging session has concluded, the user may wish to move the imaging system 10 to a left-most position with respect to patient bed 26. The position may be programmed into the motion control 51 and may require movement in both the x and y directions, per the axes depicted in FIGS. 1 and 10. This may be accomplished using the keyboard or function buttons 12 available to the operator, the touch screens of the display devices 11a, 11b, a joystick 14 or a predetermined applied force and direction to the handles 17, 19. The keyboard, the function buttons and the touch screen display devices may also be used to control the imaging and motion control portions, including the omni-directional wheels 62, 64.

The capabilities of the omni-wheels 62, 64 may also be used so that the system rotates the portable imaging device 10 about a specified vertical axis. This may be any convenient axis, such as a geometrical center of the imaging system 10, a particular feature or part of the imaging system 10 or its cart, a feature of a robot mounted on the imaging system, and so forth. The motion applied by the omni-wheels 62, 64 may also be proportional to the force(s) applied to the sensor(s) 101, 103, 105, 107—a light force may result in slower, more deliberate speed while a higher force or heavier touch may result in higher speeds applied by the omni-wheels 62, 64. In addition, the direction in which the forces are applied may indicate the desired direction of movement of the portable imaging device 10. The forces applied to the sensor(s) 101, 103, 105, 107 are resolved by motion control 51 into a resultant vector and moment that is used to drive each of front wheels 62 and rear wheels 64, as needed, to provide the desired motion.

We now discuss examples of movement using FIG. 10. In one example, pushing the left handle 17 forward would operate to cause the device to go forward and turn the device to the right. In another example, pushing the left handle 17 activates sensors 101, 105 to require forward movement. The sensor(s) 101, 103, 105, 107 may be strain gauges that interpret the force as applied in a particular direction for sensors 101, 105, forward, but with no force applied to sensors 103, 107. Since no force is applied to the right handle 19 and its sensors 103, 107, motion control 51 interprets the signals from the sensors 103, 107 as calling for a right turn with only a slight forward motion. Thus, the portable imaging device 10 makes a tight turn to the right with minimal forward movement via the omni-wheels 62, 64. In embodiments, all four wheels 62, 64 may move in this example to achieve a slight rightward turn movement. The wheels 62, 64 may be controlled individually so that their movements together achieve a desired movement of the movable station 60. As discussed above, this is an example of movement in a fine-tune mode. In other embodiments, only the left wheels 62, 64 may be activated or only the right wheels 62, 64, depending on the desired movement.

In another example, pushing left handle 17 to the right applies a force to sensors 101, 105, calling for rightward lateral or side movement. If no forward or backward force is applied to the sensors 101, 105 and no force is applied to right sensors 103, 107, motion control 51 interprets the signals as calling for rightward lateral movement with no forward or backward motion, still in a fine-tune mode. Accordingly, all four omni-wheels 62, 64 may make a small movement in the direction indicated, i.e., a few mm or inches to the right. In another example, the front wheels 62 may turn in a forward and leftward direction while the rear wheels 64 turn backwards and to the right to achieve a left turn or rotation in position. In another example, pushing both handles 17, 19 to the left will bring up a transport mode rather than a fine-movement mode. This may cause the imaging device 10 to move to the left, e.g., as shown in FIG. 1, to a leftward position with respect to patient bed or table 26, which is not part of the portable imaging device 10. The same may be said for pushing both handles 17, 19 forward, in an x-axis direction, to move the cart forward, now in a transport mode rather than in a fine-tune mode. Although described with reference to applying a force to specific handles 17, 19 and sensors 101, 103, 105, 107, it will be appreciated that more or less handles and/or sensors may be employed with the system. In addition, different forces and/or movements may occur in a number of different configurations in order to employ the fine-tune and/or transport modes and/or to move the portable imaging device 10 about the operating room.

The sensors 101, 103, 105, 107 used in embodiments of the present disclosure may include a great many force sensors. These include strain gauges, force-sensing resistors, piezo-electric sensors, piezocapacitive pressure sensors, piezoresistors and microelectro-mechanical systems (MEMS) micro-scale strain gauges. Typically, a force sensor possesses an electrical property that is changed when a user applies a force to the sensor. The property may be an electrical conductance, a resistance or a capacitance that increases or decreases in a predictable manner when a force is applied. Piezo-type sensors may generate a small microvoltage when a pressure is applied. The sensor may be part of an electrical circuit for detecting such a change, e.g., a Wheatstone bridge. By using an array or plurality of strain gauges or sensors, the user may fine-tune the direction of the desired force to be applied to the omni-wheels.

The sensors 101, 103, 105, 107 used in FIG. 10 and in the examples below may be used to control the wheels 62, 64 of the portable medical imaging device. Examples of such techniques are depicted in FIGS. 11A and 11B. In FIG. 11A, the movable station 60 is depicted with front wheels 62 and rear wheels 64, which may be the same or may be different. In this embodiment, motor 1100 under the direction of the motion control module 51, transmits power to each of the wheels as desired. The power supplied to the wheels 62, 64 may include manual operation, automatic operation, or a combination of both. The motor 1100 may have more than one shaft to supply power to axles 1102, 1104, 1106, 1108 to individually power the omni-wheels 62, 64. This allows for fine control of each wheel 62, 64 for precise placement of the portable imaging station and the imaging equipment mounted thereon. In one embodiment, the motor 1100 and each shaft or axle 1102, 1104, 1106, 1108 may further comprise a rotary encoder or other feedback mechanism to provide positional feedback to the motion control module.

Alternatively, as depicted in FIG. 11B, movable station 60 may include a local controller 1120 for allocating power via separate motors 1122 that power independent axles 1124, 1126, 1128, 1130 to each of the omni-wheels 62, 64. It may be simpler for motion control module 51 to maintain separate control of each omni-wheels 62, 64 via its own motor. In this embodiment, each motor 1122 may include its own encoder for positional feedback, and may also include an encoder or other feedback mechanism on axles 1124, 1126, 1128, 1130. Other methods for supplying power to the wheels 62, 64 may be used. The local controller or the motion control module may contain a computer program that resolves sensor readings into commands to each of the motors 1122 and axles 1124, 1126, 1128, 1130. With this technique, the omni-directional wheels 62, 64 are individually controlled for very accurate movement by the sensors provided. Feedback from the motion, such as from the rotary encoders on the axles 1124, 1126, 1128, 1130, or by other devices, can be used to store given positions for later use in restoring the movable station to a desired location.

The sensors 101, 103, 105, 107 used to sense a desired direction of the portable medical imaging system 10 may be mounted in the handles 17, 19, as disclosed above. The sensors 101, 103, 105, 107 may alternatively be mounted in a joystick or in other types of handles, as disclosed in FIGS. 12A-12D. A first alternate embodiment is disclosed in FIG. 12A. In this control system 1210, a plurality of force sensors 1212, six sensors, are mounted in a circular arrangement. A user presses on a surface of the control system, activating the sensors 1212 to guide the portable medical imaging system 10 in the appropriate direction. The direction is determined by the sensors 1212 that are activated and by the amount of force or pressure applied by the user. This is the same principle used in the example above of the handles 17, 19 of the portable imaging device 10. The circular control arrangement is useful for guiding the portable imaging device in all x-y directions, in a plane. Rotation about a predetermined axis may also be achieved by pushing up or down on the joystick or by commands to the keyboard or function button inputs. For example, depressing the joystick for a few seconds may command the portable medical imaging device to rotate clockwise about the axis, while pulling upwardly for a few seconds may command a counter-clockwise rotation.

Other examples with similar modes of operation are depicted in FIGS. 12B-12D. In FIG. 12B, eight sensors 1222 are arranged elliptically for a control system 1220 that is more suggestive of forward-backward movement, x-direction, as are the side handles discussed with respect to FIGS. 1 and 10. More sensors 1222 may be used for more sensitivity to the direction desired by the operator. In FIG. 12C, control system 1230 includes six force sensors 1232 mounted in a square pattern as shown, with two sensors 1232 for forward/backward movement and also with additional sensitivity for left/right or sideways direction with a four-corner distribution of the remaining four sensors 1232. FIG. 12D depicts an example of a control system 1240 configured with a plurality of sensors 1242 in a rectangular arrangement. This arrangement includes three sensors 1242 per side, allowing for finer tuning of lateral movements of the cart or imaging station. Other configurations may be used to guide the portable medical imaging system and its omni-directional wheels 62, 64.

Figure 13:
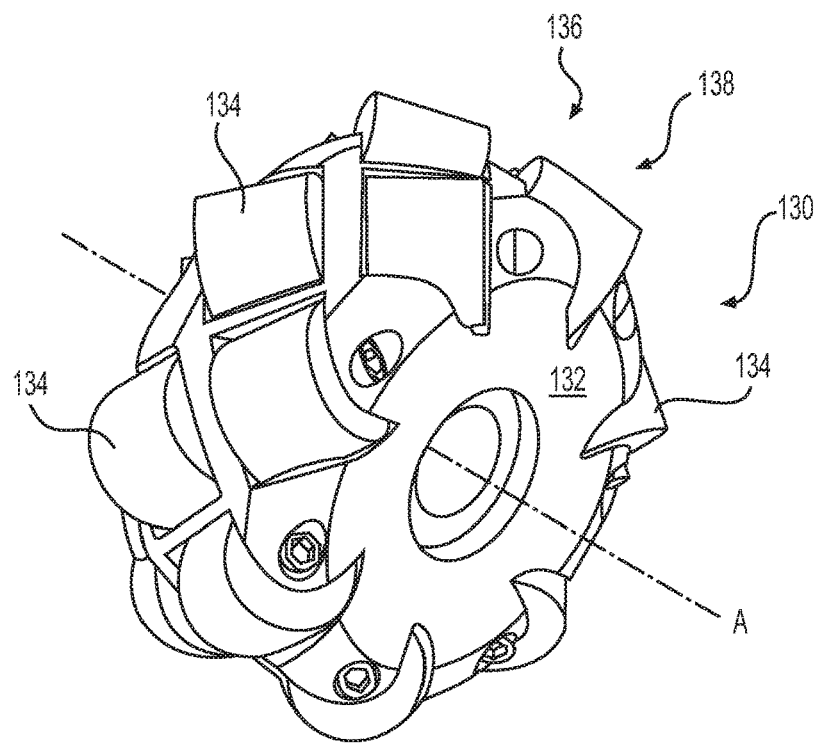
FIG. 13 is a perspective view of an example of a first omni-directional wheel ("omni-wheel") useful in imaging systems according to the present disclosure.

There are many types of omni-wheels 62, 64 useful in embodiments of the present disclosure, such as those depicted in FIGS. 13-16. Unlike traditional wheels, which only allow a device to move in one direction (e.g., forward and backward), the omni-directional wheels allow the portable imaging device to be moved in every direction (e.g., forward, backward, left, right, diagonally, in an arc, or the like). Thus, the omni-direction wheels 62, 64 allow the portable imaging device to be moved in any direction. Omni-directional wheels 62, 64 or Mecanum-type wheels generally have a central hub with a plurality of smaller wheels or rollers on its circumference. The smaller wheels are mounted at an angle to the central axis of the hub, such as 45 degrees or 90 degrees. FIG. 13 depicts an omni-directional wheel 130. This wheel 130 includes a central hub 132 about a central axis A, with a plurality of rollers or wheels 134 mounted in two non-coaxial rows 136, 138 at about a 45-degree angle to the central axis. The wheels or rollers 134 take turns being on the ground, making turning easier. These types of wheels 130 are described in U.S. Pat. Appl. 2010/0187779, which is hereby incorporated by reference in its entirety.

Figure 14:
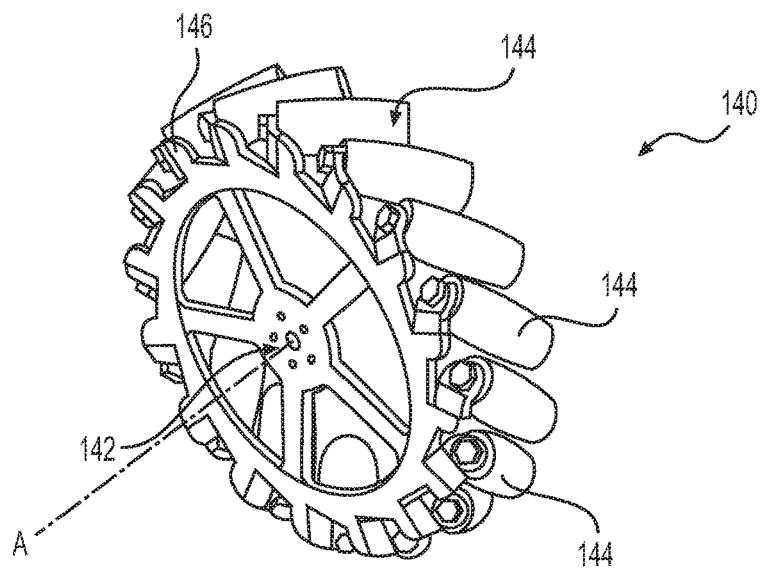
FIG. 14 is a perspective view of an example of a second omni-wheel useful in the present disclosure.

Another type of omni-directional wheel 62, 64 useful in the present disclosure is depicted in FIG. 14. Mecanum wheel 140 has a central hub 142 with a central axis A. A plurality of rollers 144 are mounted on flanges 146 on the periphery of the central hub. In this example, the flanges 146 are bent at about a 45-degree angle and thus the rollers 144 are also mounted at about a 45-degree angle to the central axis. Other angles may be used. Each wheel 62, 64 may be powered individually to guide the portable medical imaging cart in the desired direction. These types of wheels 140 are described in U.S. Pat. Appl. 2013/0292918, which is hereby incorporated by reference in its entirety.

Figure 15:
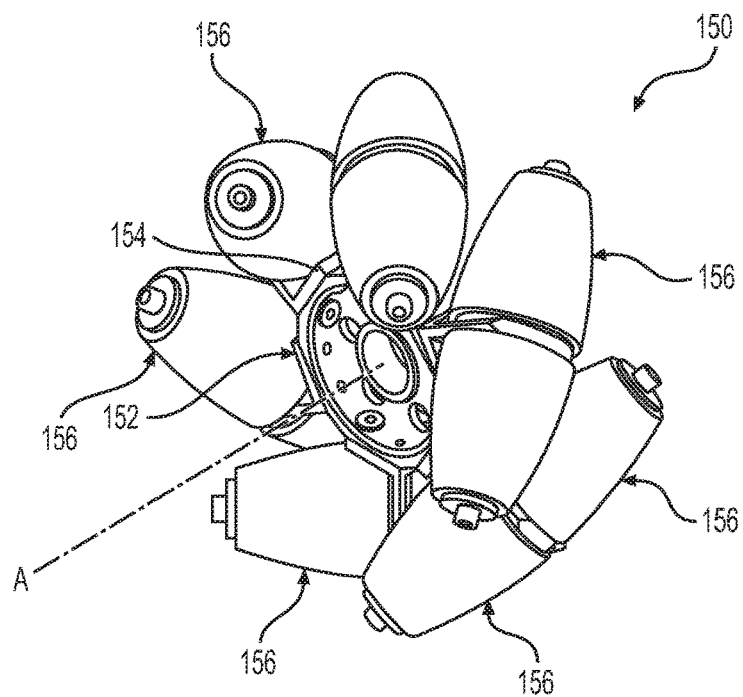
FIG. 15 is a perspective view of an example of a third omni-wheel useful in the present disclosure.

FIG. 15 depicts another type of omni-directional wheel 62, 64, a Mecanum wheel 150, useful in the present disclosure. Wheel 150 includes a central hub 152 with a central hub axis A and a plurality of flat circumferential surfaces (not shown). Each surface mounts a protruding spoke 154, which is then used to mount a circumferential roller 156. In this wheel 150, only one or two of the rollers 156 is on the floor or surface at a time, making turning easier. These types of wheels 150 are described in U.S. Pat. No. 8,011,735, which is hereby incorporated by reference in its entirety.

Figure 16:
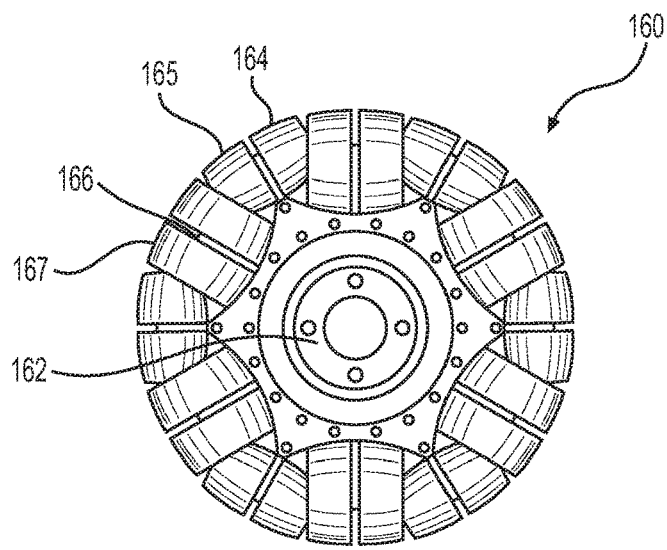
FIG. 16 is an elevational view of an example of a fourth omni-wheel useful in the present disclosure.

Yet another type of omni-directional wheel 62, 64, wheel 160 is disclosed in FIG. 16. Wheel 160 includes a central hub 162 which mounts two series of spokes or mounts 164, 166. Each of the first series of spokes 164 mounts a wheel 165 whose axis of rotation is ninety-degrees opposed to a direction of rotation of wheel 160 and central hub 162. Each of the second series of spokes 166 mounts a wheel 167 whose axis of rotation is also ninety-degrees opposed to a direction of rotation of wheel 160. Second series 166 of wheels have a slightly larger diameter than the first series 164 of wheels. Wheel 160 can rotate about an axis (not shown) perpendicular to its central hub 162. Rollers 165, 167 allow the wheels to easily change direction, thus making this a suitable omni-wheel 62, 64. These types of wheels 160 are described in U.S. Pat. Appl. 2015/0130260, which is hereby incorporated by reference in its entirety. Other types of Mecanum or omni-directional wheels 62, 64 may also be used in embodiments of this disclosure.

Once the location of the portable imaging device 10 is set in the operating room, the portable imaging device 10 may be locked into position. For example, the omni-directional wheels 62, 64 may be locked such that they are unable to move. In the alternative, a kickstand or other locking mechanism may be employed to prevent movement of the portable imaging device 10. Once the locking mechanism is released, the portable imaging device 10 is again free to move in any direction as described herein.

The advantages of this disclosure include the ability to accurately position large equipment in any desired position or direction, using the three-axis, three-degrees of freedom capabilities described above. The on-board GPS system may also be used to track the position of the equipment and to store and recall positions where the equipment is used. The unique three-axis motion capability of the omni-wheels 62, 64 includes a vertical rotary axis, which may be chosen as desired. By using both motion control and imaging control, the operator or diagnostic person can coordinate the position of the system with the desired position of the imaging equipment. The gantry position, as noted above, may be made via a robotic arm control or manual control. The precise positioning made possible by the motion control system, the encoders and the omni-wheels 62, 64 allows the portable imaging system 10 to have the control and precision of a fixed, non-mobile system.

The motion control system, the sensors, the encoders and the system memory allow the portable medical imaging system to act as a smart system. The sensors allow one to position the system as desired using the sensors and the memory. The system includes capabilities for precise, small movements for a particular image of a patient, as well as a transport mode, e.g., for moving to another patient or to another room. This allows users to park the system in a more convenient location and then to recall the imaging system to a precise location when desired. The system's memory gives users the ability to quickly and accurately recall the imaging cart to a particular position when it is needed later. The system may also use a series of fine movements to take a series of images for later combining, e.g., to stitch images together for a larger field of view. When a robot or robotic arm is used to position the imaging devices on the movable station, the ability of the station to quickly and accurately restore its position adds to the capability of the robot or robotic arm and can be considered to add a range of motion to such medical robots.

The foregoing makes it clear how the degrees of freedom of the portable medical imaging system 10 are helpful in positioning the system and in capturing images. The ability to simultaneously move both the signal transmitter and the sensor, for example by rotating them in an arc, allows rapid scans, that is, computerized tomography. The ability to simultaneously translate the signal transmitter and sensor, that is, in the x-y plane as described above, allows the system to also capture images of larger objects or an increased field of view. As shown in FIG. 17A, for example, the imaging system 170 may include an inner arm 171 mounting a signal transmitter 174 and a detector or sensor 176, for example, directly opposite from one another. As described above, the transmitter 174 and sensor 176 are mounted so that they are at opposed ends of a 180-degree arc. Thus, upon 360 degree rotation of the gantry, for example, described with reference to FIGS. 9A-9G, the area of 172 is completely imaged by the imaging device.

The radius of the inner arm 171 allows scanning of object 172, a portion thereof, or a focal point within the boundary defined by object 172. The midpoint of object 172 is centrally located between the transmitter 174 and the sensor 176. As shown in FIG. 17A, the divergence or width of the signal or x-ray beam 175 from its source 174 is sufficient to capture all aspects of the target or object 172 or a portion of an object contained within the radius defined by 172. Thus, in FIG. 17A, the field-of-view (FOV) of the signal or x-rays transmitted from transmitter 174 is able to capture all portions of target or object 172 or a portion of an object contained within the radius defined by 172. It will be appreciated that the object, in some instances, may indeed be larger than the area identified as object 172. The sensor 176, as shown here, is also sufficiently large to capture x-ray or other signals received from the transmitter 174 and transmitted through the object 172 or a portion thereof whose image is desired.

On occasion, there may be a need to image a target or object that is larger than the field-of-view depicted in FIG. 17A. Thus, as shown in FIG. 17B, object 178 is larger than the width 175 of the signal. However, by moving the location of the transmitter 174 and sensor 176 off-center, upon the 360 degree rotation of the gantry (see e.g., FIGS. 9A-9G illustrating the movement in 60 degree increments), a larger field of view encompassing the entire object 178 is obtained. As shown in FIG. 17B, the signal transmitter 174 and detector or sensor 176 are both moved off-center a specific distance 177. In this example, the distance moved, or offset, is sufficient so that the field of view of the transmitter 174 now captures the entirety of the target or object 178 as the inner arm 72 of the gantry is rotated. Again, it will be appreciated that the object may actually be larger than the portion identified as 178. In this example, the portable medical imaging cart did not move, e.g., translate, rather the signal transmitter 174 and the detector or sensor 176 are in a fixed position at distance 177 from the center line or are translated to off-center the required distance 177. By offsetting the distance 177 of the transmitter 174 and sensor 176, it was discovered that the larger field of view could be obtained without the need for rotation about a focal spot at the center of the object to be imaged and without the need for a traditional O-shaped gantry. It will be appreciated that the location of the transmitter 174 and sensor 176 may be fixed in this position or may be movable, for example, along a translation device as described in more detail below.

FIGS. 17A-17B thus depict an additional degree of freedom, the ability of the signal transmitter 174 and the detector or sensor 176 to translate, for example, in a linear fashion. FIGS. 18A-18B depict examples of at least one way this can be accomplished. In FIG. 18A, the signal transmitter 174 is mounted on a track, linear actuator, or other translational device 184. For example, the translational device 184 may be mounted in a linear track 182. In a similar manner, on the other side of arm 171, located 180-degrees opposite, the sensor or detector 176 is also mounted on a track, linear actuator, or other translational device 188, for example, in a track 186. As depicted by the arrows and phantom-line representations, the signal transmitter 174 and the detector or sensor 176 are capable of moving in a single axis, left and right. Thus, the transmitter 174 and sensor 176 are able to be positioned off-center in order to increase or narrow the field of view of the imaging space.

The linear axis provided by the translational devices 184, 188 may be oriented as desired by the user, thus providing for more precise control in virtually any desired orientation. Just as a rotary axis can be more precise than using two linear axes, this new axis may be placed as desired by orienting the gantry 56, the outer arm 70, the inner arm 72, gantry vertical shaft 59 z-axis, and even the movable station 60, in a desired orientation. Thus, as shown in FIG. 17B and in FIGS. 18A-18B, and with reference to FIG. 1 the axis is placed along the x-axis, with translation forward and backward or along the y-axis with translation left and right. With respect to FIG. 3, with transmitter 74 and sensor 76 will move up and down, along the z-axis. With respect to FIG. 4, with the gantry 56 now oriented horizontally, the new axis will also translate parallel to the x-axis as shown. In addition, the gantry and outer arm 72 are positioned in a variety of non-horizontal and non-vertical orientations in FIGS. 9B, 9C, 9E and 9F. Translational devices 184, 188 thus form an independent degree of freedom along what may be termed an intermediate or otherwise desired orientation. The transmitter 174 and sensor 176 may thus be advantageously oriented to image a particular injury, tumor, or other medical phenomenon with a larger field of view than traditional imaging devices.

The transmitter 174 and sensor 176 may be moved or adjusted as desired to use the larger field of view that is now possible. For example, the transmitter 174 and sensor 176 may be rotated in sequence to several positions to ensure complete coverage of the desired area or volume of the target. The "targeting" may be done before imaging. The desired positions may be noted and recorded in the memory 44 or in other memory available in the imaging control module 54. When the images are taken, the imaging operator or health-care professional need only sequence through the desired series of images. This can ensure complete and accurate coverage, the rotations or movements accomplished after each image is taken, so that the images are not blurred.

Translational devices or linear actuators may include motorized electric linear actuators, linear tracks, linear slides, ball slides, rack slides, ball screws, and the like to provide movement along a straight line. Translational devices 184, 188 may be controlled by the motion control module 51, thus ensuring coordinated movement of all components of the portable medical imaging device. In particular, the movements of translational devices 184, 188 may be controlled so that they are identical. Thus, when either device moves to the left or to the right, the other may also move in a coordinated manner, thus ensuring coverage of the object 178 to be imaged and also ensuring that signals sent from transmitter 174 will be captured by sensor 176 after traversal through the patient or other object to be imaged. This also prevents any escape of harmful radiation and limits exposure of the patient and diagnostic and health-care workers. The movements of the signal transmitter 174 and detector or sensor 176 are coordinated and controlled, as are the other movements of devices under the control of the motion control module. In this embodiment, each linear actuator, ballscrew or motor may include its own encoder for positional feedback, as described above for other motors or actuators of the portable medical imaging system 10.

In an alternative embodiment, the transmitter 174 and/or sensor 176 may be fixed in position. For example, transmitter 174 and sensor 176 may be fixed in position at distance 177 from center such that the equipment always images with the enlarged field of view. In another embodiment, if the area of the sensor 176 is large relative to the transmitter 174, then the sensor 176 may be stationary even if the transmitter 174 moves or translates so long as the sensor 176 is still able to detect the transmissions of the transmitter 174.

The translational movement, depicted in FIGS. 17A-17B and 18A-18B, may ensure coverage of the object to be imaged. Without such coordination and enhanced field of view capabilities, a much larger imaging device would be required. That is, the C-arms 70 and 72 would need to have a much larger diameter for complete coverage of the object 178 to be accomplished. Without the separate movements of outer C-arm 70 and inner C-arm 72, the portable imaging device might actually need a complete circle, an O-shaped gantry or gantry mount, to achieve complete 360-degree coverage. For example, some prior art devices, such as those in U.S. Pat. No. 7,108,421 achieve coverage of larger objects by rotating a larger translating apparatus to different positions about the object. The larger motion can require an O-shaped gantry or gantry mount, for example, at greater expense, with greater limitations for freedom of movement, and limitations in the operating room environment.

In contrast, embodiments of the present disclosure are able to cover larger objects and have a much larger field of view to be imaged by using small movements of the portable medical imaging system and its components. Examples of movements will be made with reference to FIGS. 1, 3 and 4. In FIG. 1, for example, gantry 56 is in a generally vertical orientation, with C-arms 70, 72 positioned about patient bed 26, ready for a patient. Imaging transmitter 74, below the patient, will work in coordination with detector 76, above the patient. The example discussed with reference to FIGS. 18A-18B requires movement in the left-right or horizontal direction, i.e., in the plane of the arm 171. With reference to FIG. 1, it can be seen that this is movement in the y-axis direction.

Figure 4:
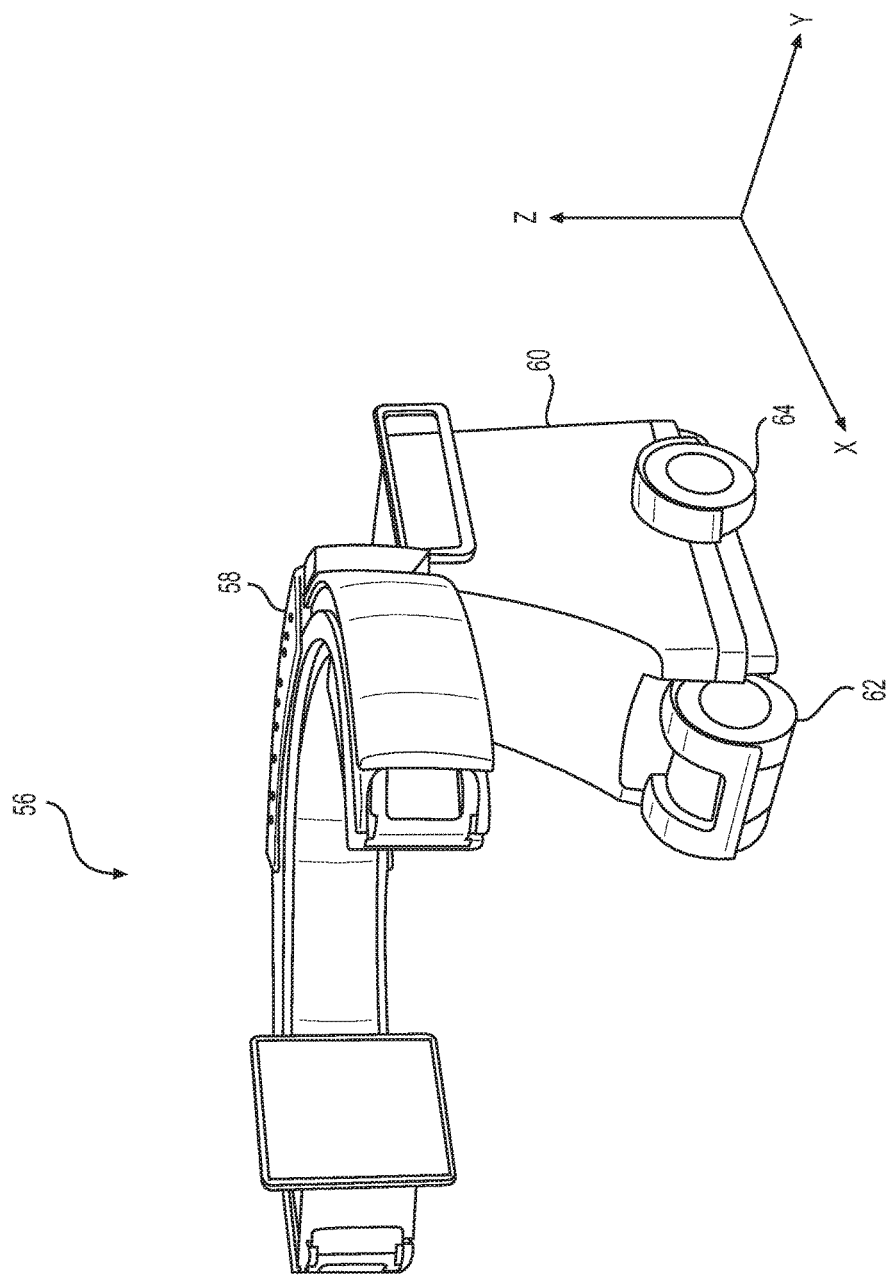
FIG. 4 is a perspective view of the imaging system of FIG. 1 in which the gantry has been rotated about the X-axis by 90 degrees.

In FIG. 3, the gantry 56 is in the same vertical orientation, but the inner arm 72 has rotated ninety-degrees, so that the transmitter 74 and sensor 76 are now oriented horizontally. This is the "rotor" rotational degree of freedom, parallel to the y-axis, previously discussed. Translating the transmitter 74 and sensor 76 in the plane of arm 72 now would be vertical movement, i.e., along the z-axis as shown in FIG. 3. With reference to FIG. 4, the gantry 56 has now rotated ninety-degrees to a horizontal position. If inner arm 72 were equipped with the linear translational devices of FIGS. 18A-18B, transmitter 74 and sensor 76 would translate within the plane of inner arm 72 in the x-axis direction depicted in FIG. 4. Rotation about the x-axis, or parallel with the x-axis, is the "tilt" degree of freedom discussed above. Thus, while the transmitter 74 and sensor 76 themselves have only a single degree of freedom, along one linear axis, that axis may be used in the context of the portable medical imaging system. Thus, the linear movement may be across a width of a patient, per FIGS. 1 and 4, or vertically up and down with respect to a patient, per FIG. 3.

With reference to these same figures, the other degrees of freedom as previously discussed, may also be considered. Thus, in FIG. 1, the outer 70 and inner 72 arms allow rotational degrees of freedom about the patient bed 26. Vertical shaft 59 allows vertical translation, i.e., linear movement along the z-axis. The omni-wheels 62, 64 allow complete freedom of movement within the x-y plane. These degrees of freedom may also be used when the medical team wishes to capture images of the patient to be mounted on patient bed 26. The portable medical imaging system 10 thus allows the six-degrees of freedom previously discussed, and also has a new linear-axis degree of freedom, as shown in FIGS. 17A-17B.

These degrees of freedom allow for additional uses of the portable medical imaging system. For example, smaller and more precisely controlled movements along the axes may now be used, rather than larger movement. For example, and as shown in FIGS. 17A-17B, if the object to be imaged is larger than can be conveniently handled, the linear degree of freedom arising from the translational movement, thereby enables an enlarged field of view.

Previously known approaches for CBCT (cone beam 3D imaging or cone beam computer tomography), also referred to as C-arm CT, undesirably produce low-contrast resolution images of brain matter and other soft tissues. Low-contrast resolution images of a brain make it difficult or not possible to visually differentiate between brain matter and the cerebrospinal fluid (CSF) in the brain ventricles. One reason these known approaches result in low-contrast resolution images is that they use large X-ray cone beam angles. Large beam angles result in high levels of X-ray scatter across the detector panel which decreases the detector's signal-to-noise ratio and, in turn, lowers the quality of the resulting image data and their usability.

Figure 19A:
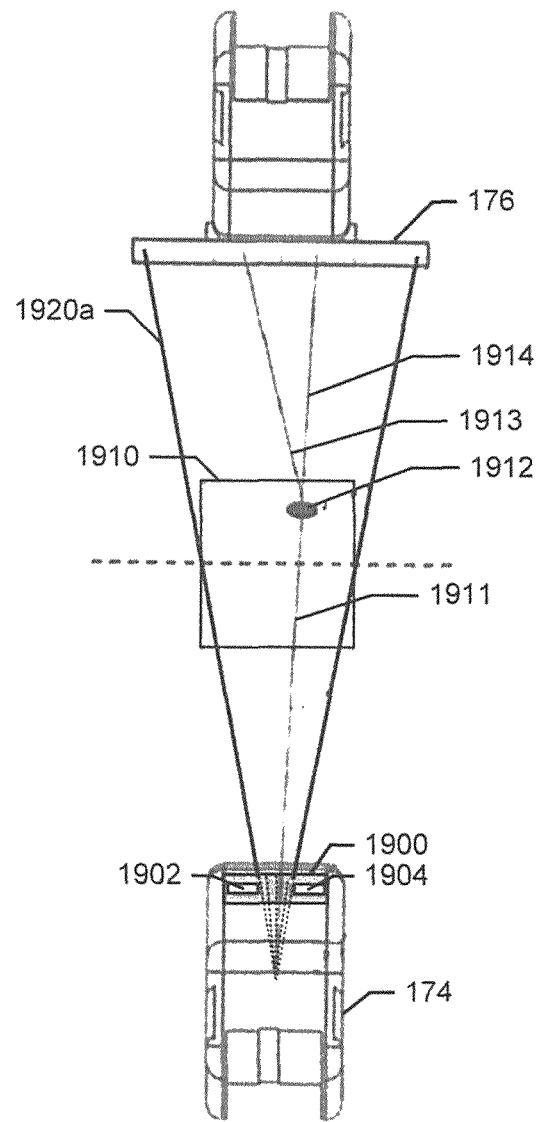
FIGS. 19A-19B depict components of a medical image system having a collimator that can produce a wide angle X-ray beam and can further produce a narrow X-ray beam that is scanned across a detector panel to provide image slices having reduced X-ray scatter effects in accordance with some embodiments of the present disclosure.

FIG. 19A depicts part of a medical image system having a collimator 1900 that can produce a wide angle X-ray beam 1918 from an X-ray beam transmitter 174 to image the entirety of a target area 1910 using a detector panel 176. The target area 1910 is shown as a 90° rotated plan view. An object 1912 within the target area 1910 is impacted by X-rays along pathway 1911, and some of the X-rays desirably pass through the object 1912 along pathway 1914 to impact the detector panel 176. However, the object 1912 also undesirably scatters some of the X-rays along pathway 1913 to impact the detector panel 176 at a spaced apart location from pathway 1914, and which decreases the detector's signal-to-noise ratio at the impact location of pathway 1913.

Various embodiments herein are directed to configuring the X-ray beam transmitter 174 to produce a more narrow angled X-ray beam that is scanned across the target area 1910 and the detector panel 176, which reduces the effect of scatter on the detector's signal-to-noise ratio and, thereby, produces high quality images. The X-ray beam transmitter 174 and the detector panel 176 are repetitively spun at least partially around the target area 1910 to generate a sequence of image slices, and the narrow angled X-ray beam is incrementally shifted a defined distance laterally across the target area 1910 between each spin. An image of the target area 1910 is generated from a sequence of image slices that are each formed from a more narrow X-ray beam that covers only a portion of the target area 1910. Scattered X-rays that impact a portion of the detector panel 176 that is outside a present image slice are ignored. The sequence of image slices are then combined to form an image of the target area 1910. Separating the image scan into smaller slices thereby reduces the negative effects of X-ray scatter, which enables higher quality low-contrast imaging. Such low-contrast imaging is particularly beneficial for generating visual images of the structure of brain matter.

With further reference to FIG. 19A, the portable medical imaging system may correspond to the system 10 in FIG. 1 and/or 56 in FIG. 3. The imaging system has a movable station 60 (FIGS. 1 and 3) with a c-arm 72 (FIG. 1) having a first end and a second end that are movable along an arc, e.g., directions 98-99 in FIG. 5. The detector panel 176 is attached to the first end of the movable c-arm 72. The X-ray beam transmitter 174 generally faces the detector panel 176 and is attached to the second end of the c-arm 72 or 70 (FIG. 3).

In accordance with various embodiments herein, the X-ray beam transmitter 174 contains a collimator 1900 that forms a window, e.g., 2050 in FIG. 20, which shapes an X-ray beam transmitted therethrough toward the detector panel 176. The collimator 1900 is configured to move a location of the widow in a lateral direction across the arc direction, e.g., direction 98-99 in FIG. 5. A controller 2200 (FIG. 24) is configured to control movement of the window by the collimator 1900 to steer the X-ray beam laterally across the detector panel 176.

Figure 19B:
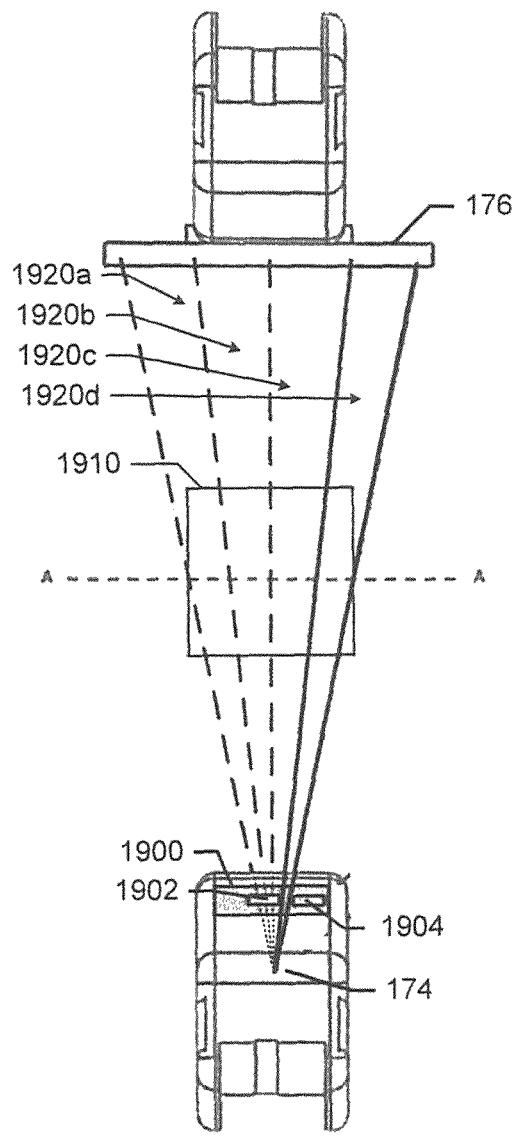

FIG. 19B depicts the medical image system of FIG. 19A with the collimator 1900 being controlled by the controller 2200 to produce a narrow X-ray beam that is incrementally scanned across the target area 1910 and the detector panel 176 to provide image slices 1920a, 1920b, 1920c, 1920c having reduced X-ray scatter effects in accordance with some embodiments of the present disclosure.

Figure 20A:
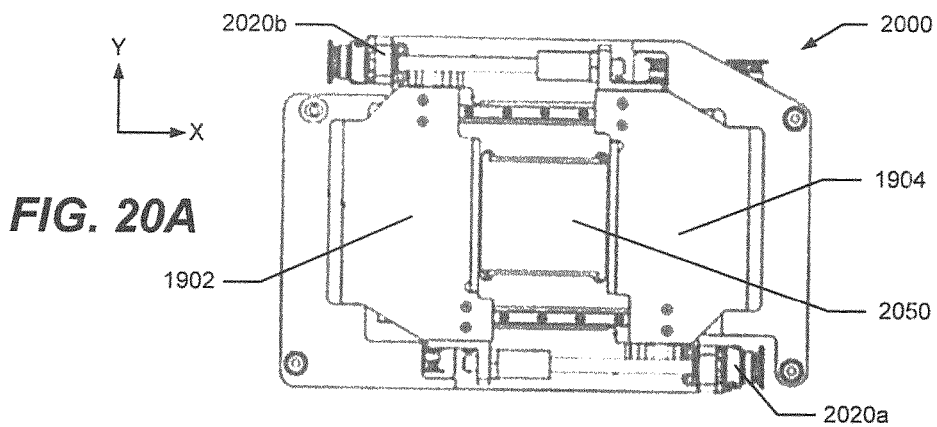
FIGS. 20A-D depict an X-axis beam collimator of an X-ray beam transmitter that is configured according to some embodiments of the present disclosure.
Figure 20B:
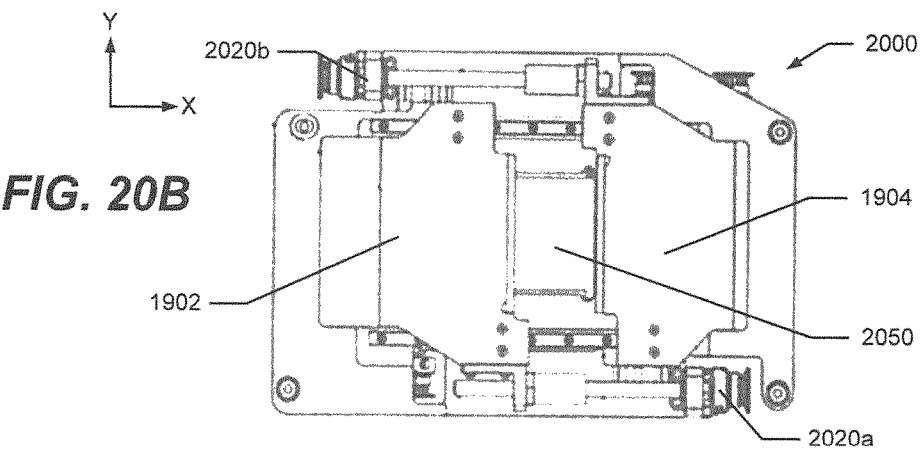
Figure 20C:
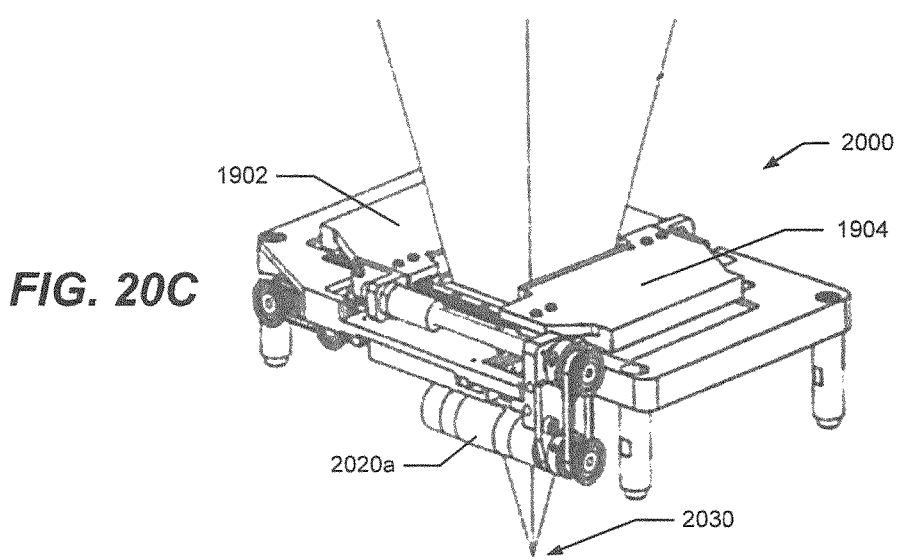
Figure 20D:
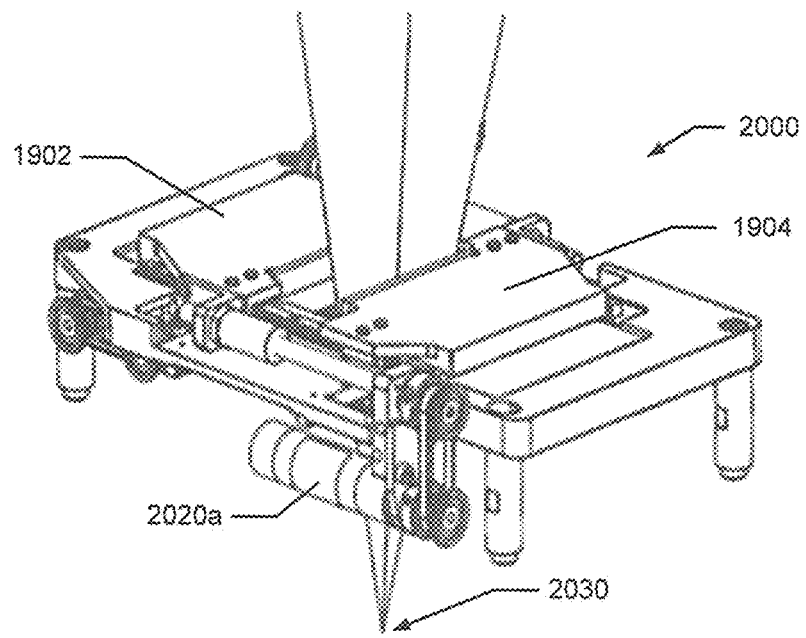
Figure 21:
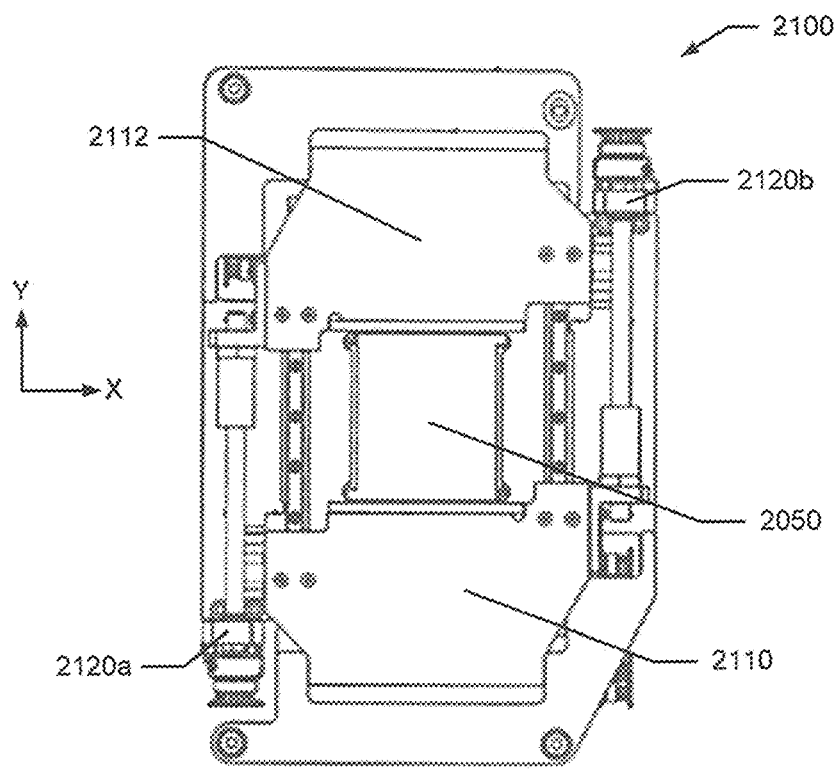
FIG. 21 depicts a Y-axis beam collimator of an X-ray beam transmitter that is configured according to some embodiments of the present disclosure.

FIGS. 20A-D depict an embodiment of an X-axis beam collimator 2000 that may be used in the collimator 1900 to adjust the size of the X-ray beam in the X-direction, e.g., laterally relative to the direction of the arc, and to scan the X-ray beam along the X-direction. FIG. 21 depicts a Y-axis beam collimator 2100 that may be used in the collimator 1900 to adjust the size of the X-ray beam in the Y-direction, e.g., along the direction of the arc, and to scan the X-ray beam along the Y-direction. The X-axis beam collimator 2000 may be stacked on the Y-axis beam collimator 2100, or vice-versa, with their windows aligned and oriented to shape the X-ray beam emitted by an X-ray source 2030 (FIG. 20C).

The X-axis beam collimator 2000 includes a pair of shutters 1902 and 1904 that are on opposite sides of a window 2050*a*, and which each have an edge surface that forms an opposing edge of the window 2050*a* in the lateral direction (e.g., X-direction). The shutters 1902 and 1904 are formed from a material, such as lead, that substantially blocks X-rays. Motor mechanisms 2020*a* and 2020*b* are connected to slide a respective one of the shutters 1902 and 1904 along tracks extending in the lateral direction to change the locations of opposing edges of the window 2050*a*. The controller 2200 (FIG. 24) controls the motor mechanisms 2020*a* and 2020*b* to set the lateral distance between the shutters 1902 and 1904 to control width of the X-ray beam in the X-direction, and further controls the motor mechanisms 2020*a* and 2020*b* to move the window 2050*a* in the X-direction to steer the X-ray beam across the detector panel 176.

Similarly, the Y-axis beam collimator 2100 includes a pair of shutters 2110 and 2112 that are on opposite sides of a window 2050*b* and which each have an edge surface that forms an opposing edge of the window 2050*b* in the arc direction (e.g., Y-direction). The shutters 2110 and 2112 are formed from a material, such as lead, that substantially blocks X-rays. Motor mechanisms 2120*a* and 2120*b* are connected to slide a respective one of the shutters 2110 and 2112 along tracks extending in the Y-direction direction to change the locations of opposing edges of the window 2050*b*. The controller 2200 (FIG. 24) controls the motor mechanisms 2120*a* and 2120*b* to set the distance between the shutters 2110 and 2112 to control width of the X-ray beam in the Y-direction. The controller 2200 may further control the motor mechanisms 2120*a* and 2120*b* to move the window 2050*b* in the Y-direction to steer the X-ray beam across the detector panel 176.

Operations that can be performed by the controller 2200 to sequentially scan a set of image slices that are used to generate a low-contrast image scan are further explained below. Input can be received from an operator, who is performing the scan, that defines a number of image slices (n) that are desired, e.g., a number of imaging spins, or which more generally defines information (e.g., an indicated level of low-contrast imaging sensitivity) from which the number of image slices (n) is determined. The controller 2200 determines the range of movement that will be needed by the collimator 1900 to scan a narrow X-ray beam across the target area 1910 and determines the size of the window 2500 that will be used to form a narrow X-ray beam that is projected onto the detector panel 176 to form an image slice.

The controller 2200 controls the X-axis beam collimator 2000 and/or the Y-axis beam collimator 2100 to shape the narrow X-ray beam and locate the X-ray beam at a starting position for a first imaging scan to generate a first one of the image slices. The controller 2200 can control the shutters 1902, 1904, 2110, and 2112 separately to define the X-direction and Y-direction dimensions of the respective windows 2050*a* and 2050*b* and, thereby, the associated shape of the X-ray beam projected through the target area. The controller 2200 can also control the shutters 1902, 1904, 2110, and 2112, via their respective motor mechanisms, to move them in a coordinated manner to maintain a constant distance between them, i.e., to maintain a static window size or control changes to the window size, for each of the image scans. For example, the controller 2200 can control shutters 1902 and 1904 to incrementally move the window 2050*b* in the X-direction to step-wise scan the narrow X-ray beam with a defined cross sectional area across the target area 1910 and generate a series of images slices along the X-direction. The incremental movements of the narrow X-ray beam can be paused while each of the individual image slices are generated.

Each image slice can be generated by performing a full scan about a set axis of interest, illustrated as axis "A" in FIG. 19A. A full scan can include moving the X-ray beam transmitter 174 and the detector panel 176 between spaced apart locations along the arc, where the locations may be at least 180° and may be up to 360° apart along the arc. For example, referring to FIG. 19B, the collimator 1900 is located at one end of its movable range while projecting a narrow X-ray beam through window 2050*a* and the target area 1910 along slice 1920*d* onto the detector panel 176. The X-ray beam transmitter 174 and the detector panel 176 are rotated along the arc, e.g., 98-99 in FIG. 5, to scan the narrow X-ray beam along slice 1920*d* through at least part of a cylindrical volume so that the detector panel 176 collects data from which a first 3-dimensional image slice is generated.

Responsive to a signal indicating completion of the first imaging scan, the controller 2200 controls the collimator 1900 to laterally move the window 2050*a* an incremental distance to steer the narrow X-ray beam along slice 1920*c*. The X-ray beam transmitter 174 and the detector panel 176 are then rotated along the arc, e.g., 98-99 in FIG. 5, to scan the narrow X-ray beam along slice 1920*c* through at least part of a cylindrical volume so that the detector panel 176 collects data from which a second 3-diminsional image slice is generated.

Responsive to a signal indicating completion of the second imaging scan, the controller 2200 controls the collimator 1900 to laterally move the window 2050*a* an incremental distance to steer the narrow X-ray beam along slice 1920*b*. The X-ray beam transmitter 174 and the detector panel 176 are then rotated along the arc, e.g., 98-99 in FIG. 5, to scan the narrow X-ray beam along slice 1920*b* through at least part of a cylindrical volume so that the detector panel 176 collects data from which a third 3-diminsional image slice is generated.

Responsive to a signal indicating completion of the third imaging scan, the controller 2200 controls the collimator 1900 to laterally move the window 2050*a* an incremental distance to steer the narrow X-ray beam along slice 1920*a*. The X-ray beam transmitter 174 and the detector panel 176 are then rotated along the arc, e.g., 98-99 in FIG. 5, to scan the narrow X-ray beam along slice 1920*a* through at least part of a cylindrical volume so that the detector panel 176 collects data from which a fourth 3-diminsional image slice is generated.

Although FIG. 19B has been illustrated with four image slices 1920*a*-1920*d* for ease of illustration of the associated imaging operations, any plural number of image slices (n) can be generated by the incremental movement of the collimator and associated incremental imaging slices through the target area 1910.

In this manner, the controller 2200 incrementally scans across the sections until the defined target area 1910 has been completely imaged. After the n sections have been imaged, the image data is collected by the controller 2200 and/or another processor and a back projection imaging process is performed to combine the image slices, e.g., the first through fourth 3-diminsional image slices, to generate a high resolution image of a low contrast structure such as a brain. Referring to FIGS. 19A and 19B, while imaging along slice 1920*b*, the X-rays scattered by object 1912 along example pathway 1914 would image the detector panel in the adjacent area of slice 1920*b*, which is ignored while imaging slice 1920*b*. Using a sequence of narrow images slices allows the X-rays that are scattered outside a presently imaged slice to be ignored, and which results in an increased resolution image through avoidance of much of the deleterious effects of X-ray scatter during the sequential imaging.

The distance that the controller 2200 laterally moves the window 2050*a* between each imaging scan can be automatically determined by the controller 2200 based on the distance between the collimator shutters 1902 and 1904, i.e., width of the window 2050*a*. In one embodiment, the controller 2200 controls the incremental distance that the first pair of motor assemblies 2020*a* and 202*b* incrementally move the shutters 1902 and 1904 based on a distance between the opposing edges of the window 2050 to change the number of imaging scans that are sequentially performed to incrementally scan the X-ray beam laterally across the detector panel 176.

Alternatively or additionally, the distance that the controller 2200 laterally moves the window 2050*a* between each imaging scan can be automatically determined based on a detected level of X-ray scatter from an image scan of the target area 1910. In one embodiment, the controller 2200 determines a level of scatter of the X-ray beam in the target area 1910 that is to be imaged in a next imaging scan that is to be performed, and controls the first pair of motor assemblies 2020*a* and 202*b* to set the distance between the opposing edges of the window 2050 and to control the incremental distance that the first pair of shutters 1902 and 1904 are moved based on the level of scatter that is determined. The level of X-ray scatter for the target area 1910 may be determined by analysis of the signal-to-noise ratio in image data collected from a wide-angle X-ray beam scan of the target area 1910, e.g., as shown in FIG. 19A. The determined level of X-ray scatter can then be used to determine the number of image slice scans that will be taken to generate the combined three-dimensional image, and the associated lateral incremental step distance that the narrow X-ray beam needs to be moved between each of the image slice scans. Smaller image slices can be generated across a portion of the target area that is determined to have a higher level of X-ray scatter. In contrast, larger image slices can be generated across another portion of the target area that is determined to have a lower level of X-ray scatter.

Figure 22:
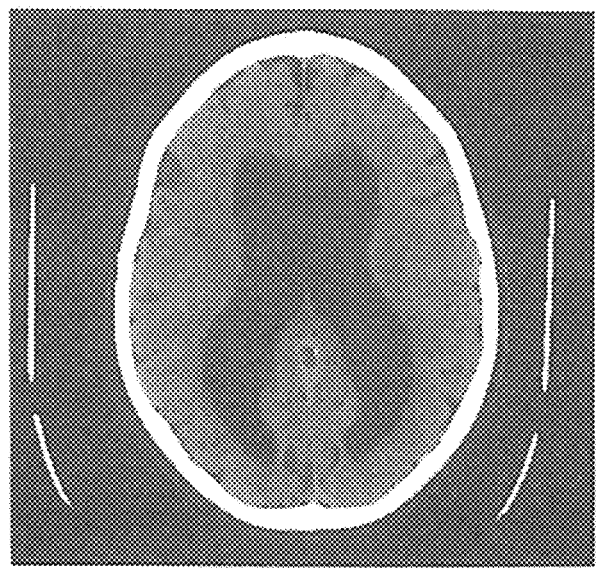
FIG. 22 illustrates an example image of brain matter that may be generated using a beam collimator that is controlled to scan a narrow X-ray beam across a detector panel in accordance with some embodiments of the present disclosure.

In one further embodiment, the controller 2200 decreases the distance between the opposing edges of the window 2050 and decreases the incremental distance that the first pair of shutters 1902 and 1904 are moved in preparation for the next imaging scan responsive to the level of scatter exceeding an upper threshold value. In contrast, the controller 2200 increases the distance between the opposing edges of the window 2050 and increases the incremental distance that the first pair of shutters 1902 and 1904 are moved in preparation for the next imaging scan responsive to the level of scatter being less than a lower threshold value FIG. 22 illustrates an example imaging scan of the ventricles of a brain (visible in the darkened section toward the middle) that may be provided by the operations described regarding FIG. 19B to scan a narrow X-ray beam across the imaged brain. It is noted that the imaging scan shows good contrast resolution. The pixel values of the image are proportional to the X-ray beam strength. Attenuation is measured in Hounsfield Units, or HU. When viewed in terms of HU, the soft tissue of brain matter has an HU value of +100 to +300 HU. HUs do not apply to CBCT scanning because the grayscale value of a voxel differs according to distance from the X-ray source, regardless of the type of material that is imaged. However, the example imaging scan highlights the importance of low-contrast imaging resolution that enables differentiation between grayscale shades when imaging low contrast tissue structures, such as brain matter.

Figure 23:
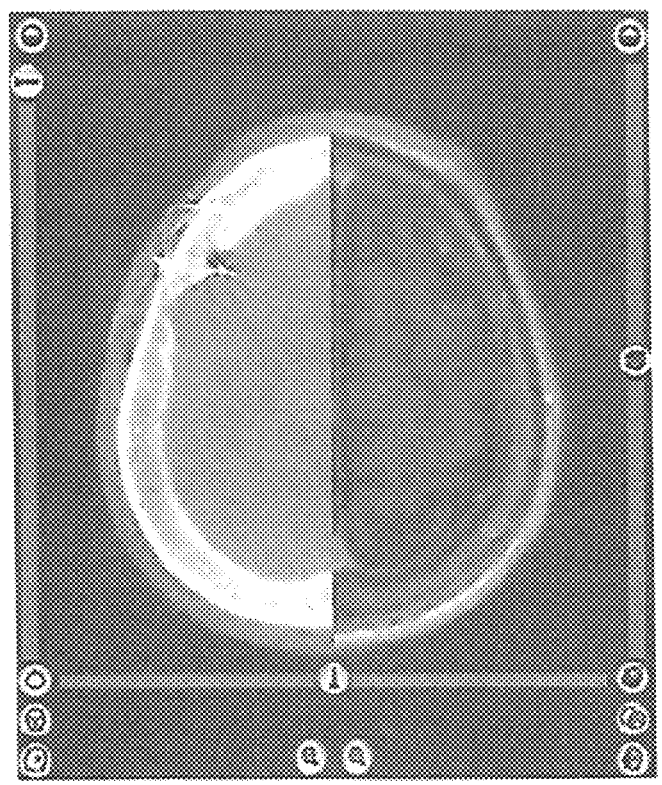
FIG. 23 illustrates two half-images of a brain, with the left half-image that may be generated using a wide angle X-ray beam and the right half-image that may be being generated by controlling a beam collimator to scan a narrow X-ray beam across a detector panel in accordance with some embodiments of the present disclosure.

FIG. 23 illustrates two half-images of a brain. The left half-image may be generated using a wide angle X-ray beam, such as according to the operations of FIG. 19A. The lack of low contrast resolution in the left half-image makes the brain matter difficult to distinguish from the surrounding fluid. The right half-image may be being generated by controlling a beam collimator to scan a narrow X-ray beam across a detector panel such as in accordance with the operations of FIG. 19B. The higher quality low contrast resolution in the right half-image makes the brain matter easier to distinguish with high resolution detail relative to the surrounding fluid.

Although various embodiments have been disclosed where the controller 2200 controls the collimator 1900 to incrementally move the window 2050 between each of a plurality of imaging scans, in some other embodiments the window 2050 is moved during an imaging scan. In one embodiment, the controller 2200 controls the motor assemblies 2020*a* and 202*b* to continuously move the shutters 1902 and 1904 in a same direction along their respective tracks during an imaging scan while the X-ray beam transmitter 174 and the detector panel 176 are moved between spaced apart locations along the arc to scan the X-ray beam laterally across the detector panel 176 during an imaging scan. The resulting imaging scan may thereby generate imaging data along a helical path through the target area 1910. A potential advantage of these operations is that a single imaging scan can cover more of or the entirety of the target area 1910 while using a narrow X-ray beam that can reduce the effects of scatter on the signal-to-noise ratio of the collected image data.

In some further related embodiments, the rate of movement of the shutters 1902 in 1904 in the distance between their respective edges may be controlled based on a detected level of X-ray scatter within the target area 1910. In one embodiment, the controller 2200 determines a level of scatter of the X-ray beam in the target area 1910 that is to be imaged next during the continuing imaging scan, and controls the motor assemblies 2020*a* and 202*b* to set the distance between the opposing edges of the window 2050 and to control speed of movement of the shutters 1902 and 1904 based on the level of scatter that is determined. In one operation, the controller 2200 decreases the distance between the opposing edges of the window 2050 and decreases the speed of movement of the shutters 1902 and 1904 responsive to the level of scatter exceeding an upper threshold value. In contrast, the controller 2200 increases the distance between the opposing edges of the window 2050 and increases the speed of movement of the shutters 1902 and 1904 responsive to the level of scatter exceeding the upper threshold value.

Figure 24:
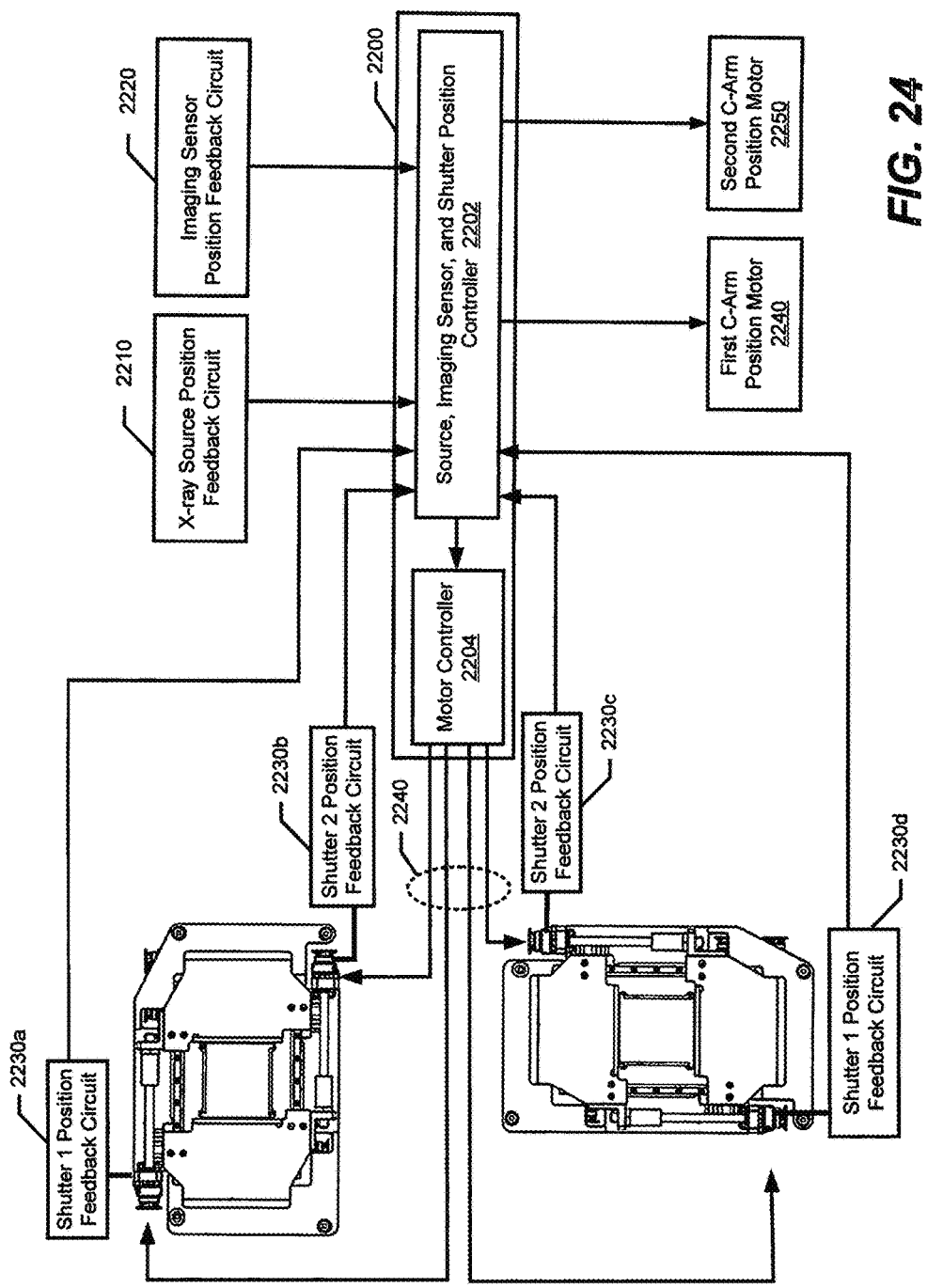
FIG. 24 is a block diagram of a control system that controls at least one of the X-axis beam collimator shown in FIGS. 20A-D and/or the Y-axis beam collimator shown in FIG. 21 to scan a narrow X-ray beam across a detector panel to provide image slices having reduced scatter in accordance with some embodiments of the present disclosure.

FIG. 24 is a block diagram of a control system that controls at least one of the X-axis beam collimator shown in FIGS. 20A-D and/or the Y-axis beam collimator shown in FIG. 21 to scan a narrow X-ray beam across a detector panel to provide image slices having reduced scatter in accordance with some embodiments of the present disclosure.

Referring to FIG. 24, the control system may be part of the portable medical imaging system, may reside within the movable station 60 (FIG. 1). The control system includes the controller 2200 which may include a source, imaging sensor, and shutter position controller 2202 and a motor controller 2204. An X-ray source position feedback circuit 2210 can measure the location of the X-ray beam transmitter 174 along the arc, and provide the location measurements to the controller 2202. An imaging sensor position feedback circuit 2220 can similarly measure the location of the detector panel 176 long arc, and provide the location measurements to the controller 2202. Shutter position feedback circuits 2230a, 2230b, 2230c, and 2230d can separately measure the locations of respective ones of the shutters 1902, 1904, 2110, 2112 along their respective tracks, and provide the location measurements to the controller 2202. The controller 2202 can separately control the motor assemblies 2020a, 2020b, 2120a, and 2120b to move selected ones of the shutters 1902, 1904, 2110, 2112 to defined locations along their respective tracks. The motor controller 2204 may convert the digital control signaling from the controller 2202 to a set 2240 of analog signals that each separately control movement of one of the motor assemblies 2020a, 2020b, 2120a, and 2120b.

Figure 25:
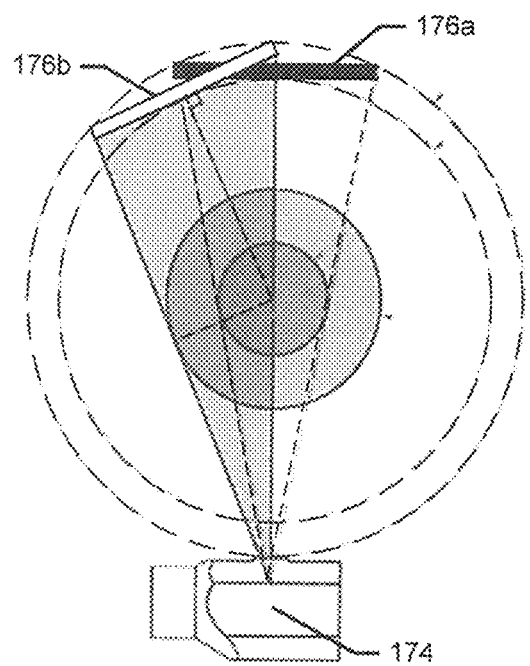
FIG. 25 depicts operations for rotating the detector panel about a focal point while maintaining the X-ray beam transmitter in a static position, in accordance with some embodiments of the present disclosure.

The field-of-view provided by an image scan through a target area can be changed by moving the location of the detector panel 176 off-center relative to the X-ray beam transmitter 174. FIG. 25 depicts operations for rotating the detector panel 176, between two locations 176a and 176b, about a focal point while maintaining the X-ray beam transmitter 174 in a static position. Moving the detector panel 176 in this manner may provide a larger field-of-view of the target area and/or may reduce the effects of X-ray scatter. An image scan may be performed with the detector panel at the first location 176a and a second image scan may be performed with the detector panel at the second location 176b, and the resulting imaging data from the two scans may be combined to reduce the effects of X-ray scatter from the imaging area and/or to increase the field-of-view of the image scan.

The c-arm may be configured to telescope its arcuate length between the connection locations of the X-ray beam transmitter 174 and the detector panel 176, to change the arc distance between them. In one embodiment, the c-arm is configured to change length by telescoping along the arc to change distance along the arc between the connected detector panel 176 and the connected x-ray beam transmitter 174. For example, with reference to FIG. 3, the x-ray beam transmitter, illustrated as 74 in FIG. 3, can be attached directed to the outer c-arm 70 and the detector panel, illustrated as 76 in FIG. 3, can be attached directed to the inner c-arm 72 so that the detector can be controllably telescoped along the arc away from and toward the transmitter by movement of the inner c-arm 72 relative to the outer c-arm 70.

Before performing an imaging scan of a cylindrical volume by movement of the X-ray beam transmitter 174 and the detector panel 176 between spaced apart locations along the arc, the controller 2200 can be configured to control telescoping movement of the c-arm to move at least one of the detector panel 176 and the x-ray beam transmitter 174 along the arc to change distance therebetween and radially shift the cylindrical volume that is imaged during the imaging scan.

The detector panel 176 may alternatively or additionally be mounted to the c-arm using the translation device 184 in FIG. 18B, which can be configured to move the detector panel 176 along a rail to provide the described rotation relative to the X-ray beam transmitter 174.

Figure 26:
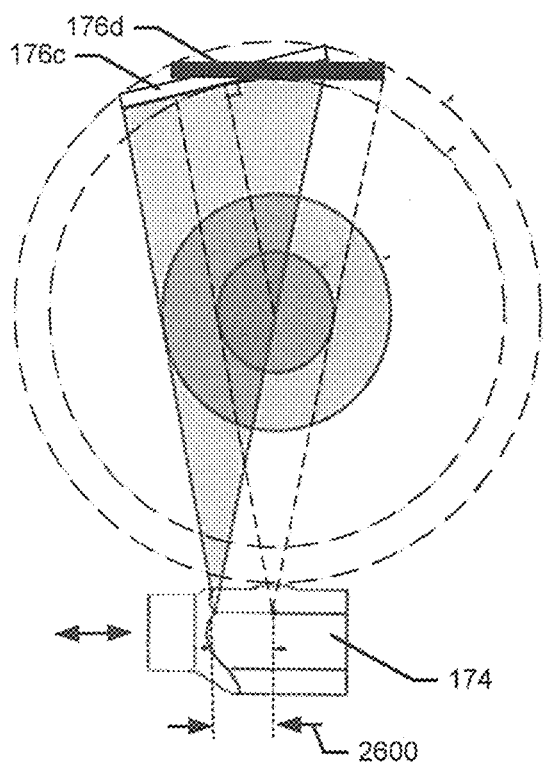
FIG. 26 depicts operations for translating the X-ray beam transmitter to radially shift the cylindrical volume that is imaged during the imaging scan, in accordance with some embodiments of the present disclosure.

Alternatively or additionally, the field-of-view provided by an image scan through a target area can be changed by moving the location of the X-ray beam transmitter 174 off-center. FIG. 26 depicts operations for translating the X-ray beam transmitter 174 to radially shift the cylindrical volume that is imaged during the imaging scan. A translation device 184 in FIG. 18B can mount the X-ray beam transmitter 174 to the first end of the c-arm and be configured to move the X-ray beam transmitter 174 along a rail. Before performing an imaging scan of a cylindrical volume by movement of the X-ray beam transmitter 174 and the detector panel 176 between spaced apart locations along the arc, the controller 2200 can be configured to control the translation device 184 to position the X-ray beam transmitter 174 in the direction to radially shift the cylindrical volume that is imaged during the imaging scan.

Some other aspects of the present disclosure are directed to enabling a human operator to visually confirm that the variable-dimension X-ray beam generated by the collimator disclosed herein will properly scan a target area. A filter ladder is connected to the collimator for use in hardening the X-ray beam by filtering out harmful low-energy X-rays. In some embodiments, a light source is connected to the filter ladder configured to be slidable to be aligned with the window 2050 project a light beam toward the target area. The light source is configured to project a light beam through the window 2050 having a similar dimensional shape to the X-ray beam to allow visual inspection of the planned imaging scan of the target area.

Figure 27A:
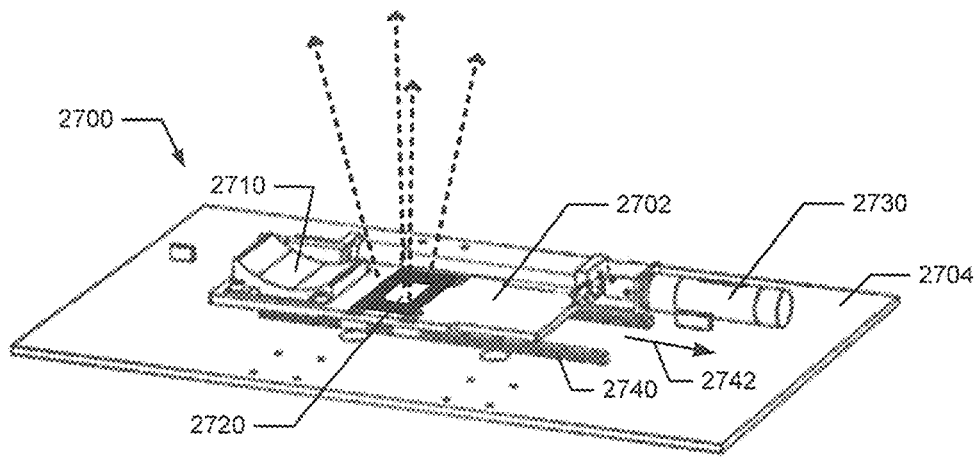
FIGS. 27A-27B depict a filter ladder that can sequentially align various X-ray filters and a light source with a window provided through the collimator of FIGS. 19-21.
Figure 27B:
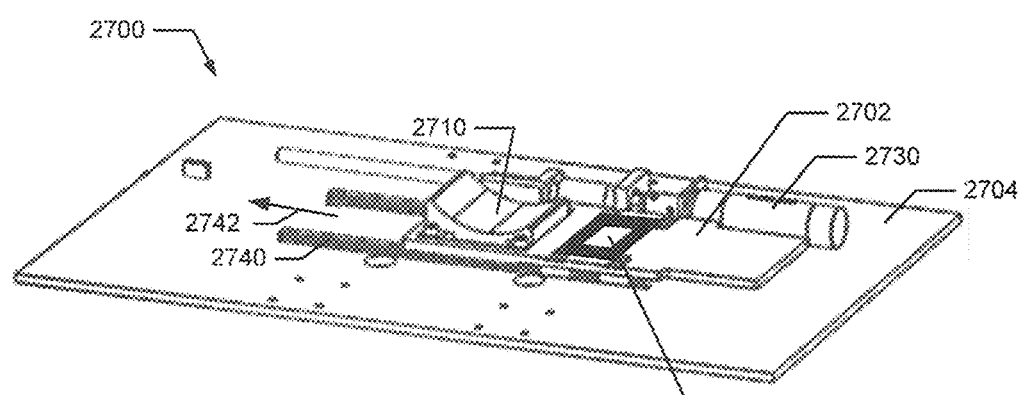

FIGS. 27A-27B depict a filter ladder 2700 that can sequentially align various X-ray filters and a light source with a window provided through the collimator of FIGS. 19-21. The filter ladder 2700 includes a support structure 2704 and a movable elongated strip 2702. The support structure 2704 is connected to the collimator 1900. The movable elongated strip 2702 is slideably connected to the support structure 2704. The filter ladder 2700 further includes a plurality of X-ray filters 2710 that are attached to the movable elongated strip 2702. The X-ray filters provide differing levels of X-ray filtering of the X-rays from the X-ray source. The X-ray filters may be formed from different types of metals and/or different thicknesses of metals. In accordance with some embodiments, a light source 2720 is attached to the movable elongated strip 2702 at a location that is spaced apart from the X-ray filters 2710. The movable elongated strip 2702 is configured to be slid across the window 2050 to sequentially align different ones of the X-ray filters 2710 and the light source 2720 with the window 2050. The light source 2720 is configured to project visible light toward the detector panel 176 when aligned with the window 2050.

The light source 2720 may include a plurality of light emitter diodes (LED) that are spaced apart to emit a light beam through the window 2050 that visually indicates on a targeted object, located between the X-ray beam transmitter 174 and the detector panel 176, the dimensions of the X-ray beam will be transmittable through the window 2050. The LEDs may be angled in spaced apart to configure the light beam, which is projected through the window 2050 onto the target area, to approximate the dimensional shape of the X-ray beam will be emitted to the target area across all of the image scans, i.e., a wide field-of-view, and/or by a single one of the image scans.

Alternatively or additionally, the light source 2720 may include a plurality of laser devices that are spaced apart and angled to collectively emit a light beam through the window 2050 that visually indicates on a targeted object, located between the X-ray beam transmitter 174 and the detector panel 176, the dimensions of the X-ray beam will be transmittable through the window 2050.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference, as if each such patent or publication were individually incorporated by reference herein. Various features and advantages of the invention are set forth in the following claims.

What is claimed is:

1. A portable medical imaging system comprising:
    a movable station comprising a c-arm having a first end and a second end that are movable along an arc relative to the movable station;
    a detector panel attached to the first end of the movable c-arm;
    an X-ray beam transmitter facing the detector panel and attached to the second end of the c-arm, the X-ray beam transmitter containing a collimator that forms a window through which an X-ray beam is transmitted toward the detector panel, wherein the collimator is configured to move the window in a lateral direction across a direction of the arc; and
    a controller configured to control movement of the window by the collimator to steer the X-ray beam laterally across the detector panel,
    wherein a filter ladder comprising a support structure and a movable elongated strip, the support structure being connected to the collimator, the movable elongated strip being slideably connected to the support structure, the filter ladder further comprising a plurality of X-ray filters each providing differing levels of X-ray filtering and attached to the movable elongated strip, and a light source attached to the movable elongated strip at a location spaced apart from the X-ray filters, wherein the movable elongated strip is configured to be slidable across the window to sequentially align different ones of the X-ray filters and the light source with the window, the lit source is configured to project visible light toward the detector panel when aligned with the window.

2. The portable medical imaging system of claim 1, wherein:
    between each of a plurality of imaging scans through which the X-ray beam transmitter and the detector panel are repetitively moved between locations along the arc, the controller controls the collimator to incrementally move the window responsive to a signal indicating completion of the one of the imaging scans.

3. The portable medical imaging system of claim 1, wherein:
    the collimator is positioned between an X-ray source and the detector panel, and comprises:
        a first pair of shutters that are on opposite sides of the window and which each have an edge surface that forms an opposing edge of the window in the lateral direction, the first pair of shutters are each slidable along respective tracks extending along the lateral direction to change locations of opposing edges of the window; and
        a first pair of motor assemblies connected to move respective ones of the first pair of opposing shutters along their respective tracks; and
    the controller controls the first pair of motor assemblies to position the first pair of shutters along their respective tracks.

4. The portable medical imaging system of claim 1, wherein:
    the c-arm is configured to change length by telescoping along the arc to change distance along the arc between the connected detector panel and the connected x-ray beam transmitter.

5. The portable medical imaging system of claim 1, wherein:
    the light source comprises a plurality of light emitter diodes arranged to emit a light beam through the window that visually indicates on a targeted object, located between the X-ray beam transmitter and the detector panel, the dimensions of the X-ray beam will be transmittable through the window.

6. The portable medical imaging system of claim 1, wherein:
    the light source comprises a plurality of laser devices spaced apart and angled to collectively emit a light beam through the window that visually indicates on a targeted object, located between the X-ray beam transmitter and the detector panel, the dimensions of the X-ray beam will be transmittable through the window.

7. The portable medical imaging system of claim 3, wherein:
    between each of a plurality of imaging scans through which the X-ray beam transmitter and the detector panel are repetitively moved between spaced apart locations along the arc, the controller controls the first pair of motor assemblies to incrementally move the first pair of shutters in the lateral direction along their respective tracks responsive to a signal indicating completion of the one of the imaging scans.

8. The portable medical imaging system of claim 3, wherein:
    the controller controls the first pair of motor assemblies to continuously move the first pair of shutters in a same direction along their respective tracks during an imaging scan while the X-ray beam transmitter and the detector panel are moved between spaced apart locations along the arc to scan the X-ray beam laterally across the detector panel during an imaging scan.

9. The portable medical imaging system of claim 3, wherein:
    the collimator further comprises:
        a second pair of shutters that are on opposite sides of the window are oriented 90 degrees offset relative to the first pair of shutters, the second pair of shutters each have an edge surface that forms an opposing edge of the window in the direction of the arc, the second pair of shutters are each slidable along respective tracks extending along the direction of the arc; and a second pair of motor assemblies connected to move respective ones of the second pair of opposing shutters along their respective tracks; and the controller controls the second pair of motor assemblies to position the second pair of shutters along their respective tracks.

10. The portable medical imaging system of claim 7, wherein:

the controller controls the first pair of motor assemblies to incrementally move the first pair of shutters a same distance in the lateral direction along their respective tracks, to maintain a constant distance between the opposing edges of the window, responsive to the signal indicating completion of the one of the imaging scans.

11. The portable medical imaging system of claim 10, wherein:

the controller controls the incremental distance that the first pair of motor assemblies incrementally move the first pair of shutters based on a distance between the opposing edges of the window to change the number of imaging scans that are sequentially performed to incrementally scan the X-ray beam laterally across the detector panel.

12. The portable medical imaging system of claim 11, wherein the controller determines a level of scatter of the X-ray beam in a target area that is to be imaged in a next imaging scan that is to be performed, and controls the first pair of motor assemblies to set the distance between the opposing edges of the window and to control the incremental distance that the first pair of shutters are moved based on the level of scatter that is determined.

13. The portable medical imaging system of claim 12, wherein the controller decreases the distance between the opposing edges of the window and decreases the incremental distance that the first pair of shutters are moved in preparation for the next imaging scan responsive to the level of scatter exceeding an upper threshold value; and the controller increases the distance between the opposing edges of the window and increases the incremental distance that the first pair of shutters are moved in preparation for the next imaging scan responsive to the level of scatter being less than a lower threshold value.

14. The portable medical imaging system of claim 8, wherein:

the controller determines a level of scatter of the X-ray beam in a target area that is to be imaged next during the continuing imaging scan, and controls the first pair of motor assemblies to set the distance between the opposing edges of the window and to control speed of movement of the first pair of shutters based on the level of scatter that is determined.

15. The portable medical imaging system of claim 14, wherein the controller decreases the distance between the opposing edges of the window and decreases the speed of movement of the first pair of shutters responsive to the level of scatter exceeding an upper threshold value; and the controller increases the distance between the opposing edges of the window and increases the speed of movement of the first pair of shutters responsive to the level of scatter exceeding the upper threshold value.

16. The portable medical imaging system of claim 4, wherein:

before performing an imaging scan of a cylindrical volume by movement of the X-ray beam transmitter and the detector panel between spaced apart locations along the arc, the controller is configured to control telescoping movement of the c-arm to move at least one of the detector panel and the x-ray beam transmitter along the arc to change distance therebetween and radially shift the cylindrical volume that is imaged during the imaging scan.

17. The portable medical imaging system of claim 16, further comprising:

a translation device mounting the X-ray beam transmitter to the first end of the c-arm and configured to move the X-ray beam transmitter along a rail; and before performing an imaging scan of a cylindrical volume by movement of the X-ray beam transmitter and the detector panel between spaced apart locations along the arc, the controller is configured to control the translation device to position the X-ray beam transmitter in the direction to radially shift the cylindrical volume that is imaged during the imaging scan.

* * * * *